United States Patent
Zapol et al.

(10) Patent No.: US 12,064,543 B2
(45) Date of Patent: Aug. 20, 2024

(54) SYSTEM AND METHOD FOR EXTRACORPOREAL CARBON MONOXIDE REMOVAL WITH PHOTOTHERAPY

(71) Applicant: The General Hospital Corporation, Boston, MA (US)

(72) Inventors: Warren M. Zapol, Boston, MA (US); Richard Rox Anderson, Boston, MA (US); Luca Zazzeron, Boston, MA (US); Walfre Franco, Boston, MA (US); William A. Farinelli, Boston, MA (US); Anna Fischbach, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 812 days.

(21) Appl. No.: 17/257,217

(22) PCT Filed: Jul. 3, 2019

(86) PCT No.: PCT/US2019/040656
§ 371 (c)(1),
(2) Date: Dec. 30, 2020

(87) PCT Pub. No.: WO2020/010286
PCT Pub. Date: Jan. 9, 2020

(65) Prior Publication Data
US 2021/0128813 A1    May 6, 2021

Related U.S. Application Data

(60) Provisional application No. 62/693,620, filed on Jul. 3, 2018.

(51) Int. Cl.
*A61M 1/36* (2006.01)

(52) U.S. Cl.
CPC ........ *A61M 1/3681* (2013.01); *A61M 1/3607* (2014.02); *A61M 1/3621* (2013.01);
(Continued)

(58) Field of Classification Search
CPC .............. A61M 1/1625; A61M 1/1623; A61M 1/1698; A61M 1/3607; A61M 1/3621;
(Continued)

(56) References Cited

U.S. PATENT DOCUMENTS

| | | |
|---|---|---|
| 5,037,610 A | 8/1991 | Fukasawa |
| 5,240,677 A | 8/1993 | Jones |

(Continued)

FOREIGN PATENT DOCUMENTS

| | | |
|---|---|---|
| CA | 1267339 A | 4/1990 |
| JP | H08131543 A | 5/1996 |

(Continued)

OTHER PUBLICATIONS

Yang, C.C. et al, Formic acid: a rare but deadly source of carbon monoxide poisoning., Clin Toxicol (Phila) 46, 287-9 (2008).
(Continued)

*Primary Examiner* — Catharine L Anderson
*Assistant Examiner* — Erin A Kim
(74) *Attorney, Agent, or Firm* — Quarles & Brady LLP

(57) ABSTRACT

Systems and methods for removing carbon monoxide from whole blood are provided. In one configuration, an extracorporeal phototherapy system includes an oxygenator and a light source configured to output light and arranged to emit the light output by the light source onto at least one surface of the oxygenator. The oxygenator includes a plurality of membrane layers each having a plurality of microporous hollow fiber membranes. The plurality of microporous hollow fiber membranes each include an external surface and an internal channel. Each of the plurality of membrane layers
(Continued)

may be rotationally offset with respect to an adjacent layer. The oxygenator further includes a gas inlet port in fluid communication with a first end of the internal channels, a gas outlet port in fluid communication a second end of the internal channels, a blood inlet port, and a blood outlet port.

19 Claims, 29 Drawing Sheets

(52) U.S. Cl.
CPC ... *A61M 1/3623* (2022.05); *A61M 2202/0233* (2013.01); *A61M 2205/3606* (2013.01); *B01D 2313/20* (2013.01); *B01D 2313/903* (2022.08)

(58) Field of Classification Search
CPC ........ A61M 1/3623; A61M 2202/0233; A61M 2205/3606; A61M 1/16; A61M 1/327; A61M 1/3681–3686; A61N 5/0613; A61N 5/067; A61N 2005/0659; A61N 2005/0662; A61N 2005/0652; B01D 2313/20; B01D 63/02
See application file for complete search history.

(56) References Cited

U.S. PATENT DOCUMENTS

| | | | |
|---|---|---|---|
| 7,601,201 | B2 | 10/2009 | Fukutomi |
| 8,858,880 | B2 | 10/2014 | Smyczynski |
| 2003/0194348 | A1* | 10/2003 | Divino, Jr. .......... A61M 1/1698 604/6.14 |
| 2012/0157905 | A1 | 6/2012 | Sehgal |
| 2015/0290385 | A1 | 10/2015 | Smyczynski |
| 2018/0140863 | A1 | 5/2018 | Zapol |
| 2019/0015578 | A1* | 1/2019 | Smyczynski ....... A61M 1/3683 |
| 2020/0069860 | A1* | 3/2020 | Rammo .............. A61M 1/3496 |

FOREIGN PATENT DOCUMENTS

| | | | |
|---|---|---|---|
| WO | 1991016967 | A1 | 11/1991 |
| WO | WO-2016187187 | A1 * | 11/2016 ........... A61B 1/2676 |

OTHER PUBLICATIONS

Yin, L. et al, Treatment of acute carbon monoxide poisoning with extracorporeal membrane trioxygenation., Int J Artif Organs 35, 1070-6 (2012).
Zanella, A. et al, Respiratory Electrodialysis: a Novel, Highly Efficient, Extracorporeal CO2 Removal Technique, Am. J. Respir. Crit. Care Med. 192, 719-726 (2015).
Zazzeron, L. et al, Pulmonary Phototherapy for Treating Carbon Monoxide Poisoning, Am J Respir Crit Care Med 192, 1191-1199 (2015).
Zazzeron, L. et al, Pulmonary Phototherapy to Treat Carbon Monoxide Poisoning in Rats, Shock 47, 735-742. 2017.
Zijlstra, W.G. et al, Absorption spectra of human fetal and adult oxyhemoglobin, de-oxyhemoglobin, carboxyhemoglobin, and methemoglobin., Clin. Chem. 37, 1633-8 (1991).
Aggarwal, N.R. et al, Targeting normoxemia in acute respiratory distress syndrome may cause worse short-term outcomes because of oxygen toxicity., Ann Am Thorac Soc 11, 1449-53 (2014).
Alarie, Y. (2002). Toxicity of fire smoke. Critical reviews in toxicology, 32(4), 259-289.
Annich, G. M., et al. "Thromboprophylaxis in extracorporeal circuits: current pharmacological strategies and future directions." American Journal of Cardiovascular Drugs 17.6 (2017): 425-439.
Brown, S.D. et al, In vivo binding of carbon monoxide to cytochrome c oxidase in rat brain., J. Appl. Physiol. 68, 604-10 (1990).
Bucher, T. et al, Photochemische spaltung des kohlenoxydmyoglobins durch ultraviolette strahlung (wirksamkeit der durch die proteinkomponente des pigments absorbierten quanten, Biochim Biophys Acta 1, 21-34 (1947). With English abstract.
Coburn, R.F. The carbon monoxide body stores. Ann. NY Acc. Sci. 174, 11-22 (1970).
Collier, C. R. (1976). Oxygen affinity of human blood in presence of carbon monoxide. Journal of Applied Physiology, 40(3), 487-490.
Dickey, B.F. et al, Oleic-acid-induced lung injury in the rat. Failure of indomethacin treatment or complement depletion to ablate lung injury., Am. J. Pathol. 103, 376-83 (1981).
Dries, D.J. et al, Inhalation injury: epidemiology, pathology, treatment strategies., Scand J Trauma Resusc Emerg Med 21, 31 (2013).
Esper, S. A., et al. "Extracorporeal membrane oxygenation in the adult: a review of anticoagulation monitoring and transfusion." Anesthesia & Analgesia 118.4 (2014): 731-743.
Fein, A. et al, Carbon monoxide effect on alveolar epithelial permeability., Chest 78, 726-31 (1980).
Fisher, J. A., et al. "Isocapnic hyperpnea accelerates carbon monoxide elimination." American journal of respiratory and critical care medicine 159.4 (1999): 1289-1292.
Gandini, C., et al. (2001). Carbon monoxide cardiotoxicity. Journal of Toxicology: Clinical Toxicology, 39(1), 35-44.
Gibson, Q.H. et al, Photosensitivity of haem compounds., Nature 180, 1416-7 (1957).
Gorguner, M. et al, Acute inhalation injury., Eurasian J Med 42, 28-35 (2010).
Haldane, J. et al, The oxygen tension of arterial blood, J. Physiol. 20, 497-520 (1896).
Hampson, N.B. et al, Practice Recommendations in the Diagnosis, Management, and Prevention of Carbon Monoxide Poisoning. Am. J. Respir. Crit. Care Med. 186, 1095-1101 (2012).
Hoffman, B.H. et al, On the photosensitivity of liganded hemoproteins and their metal-substituted analogues., Proc. Natl. Acad. Sci. U.S.A. 75, 21-5 (1978).
International Searching Authority. International Search Report and Written Opinion for application PCT/US2019/040629. Mailed on Jan. 17, 2020. 18 pages.
Jay, G.D. et al, Portable hyperbaric oxygen therapy in the emergency department with the modified Gamow bag., Ann Emerg Med 26, 707-11 (1995).
Kolobow, T. et al, The carbon dioxide membrane lung (CDML): a new concept., Trans Am Soc Artif Intern Organs 23, 17-21 (1977).
Kuz'min, VV et al, Study of photodissociation parameters of carboxyhemoglobin, Quantum Electronics 38, 695-701 (2008).
Amhaut, L. et al, A Pre-Hospital Extracorporeal Cardio Pulmonary Resuscitation (ECPR) strategy for treatment of refractory out hospital cardiac arrest: An observational study and propensity analysis., Resuscitation 117, 109-117 (2017).
Lee, H.B. et al, Blood volume in the rat., J. Nucl. Med. 26, 72-6 (1985).
Li, C.K. et al, A retrospective study on carboxyhaemoglobin half-life in acute carbon monoxide poisoning in patients treated with normobaric high flow oxygen, Hong Kong Journal of Emergency Medicine 13, 205-211 (2006).
Lim, E.K. et al, Simple citrate anticoagulation protocol for low flux haemodialysis., BMC Nephrol 19, 16 (2018).
Matute-Bello, G. et al, Animal models of acute lung injury., Am. J. Physiol. Lung Cell Mol. Physiol. 295, L379-99 (2008).
McCunn, M., et al. "Extracorporeal support in an adult with severe carbon monoxide poisoning and shock following smoke inhalation: a case report." Perfusion 15.2 (2000): 169-173.
Miro, O. et al, Mitochondrial Cytochrome c Oxidase Inhibition during Acute Carbon Monoxide Poisoning. Pharmacol. Toxycol. 82, 199-202 (1998).
Mukhopadhyay, S., et al. (2018). Surveillance of carbon monoxide-related incidents—Implications for prevention of related illnesses and injuries, 2005–2014. The American journal of emergency medicine, 36(10), 1837-1844.
Pace, N. et al, Acceleration of carbon monoxide elimination in man by high pressure oxygen. Science 111, 652-4 (1950).
Parving, H.H. et al, Effect of carbon monoxide exposure on capillary permeability to albumin and a2-macroglobulin., Scand. J. Clin. Lab. Invest. 29, 381-8 (1972).

(56) References Cited

OTHER PUBLICATIONS

Perrot, D et al, [Acute carbon monoxide poisoning: lung injury or cardiogenic pulmonary edema?]., Toxicol Eur Res 5, 181-3 (1983).
Piantadosi, C.A. et al, Carbon monoxide, oxidative stress, and mitochondrial permeability pore transition., Free Radic. Biol. Med. 40, 1332-9 (2006).
Rambaud, J. et al, A pilot study comparing two polymethylpentene extracorporeal membrane oxygenators., Perfusion 28, 14-20 (2013).
Saffran, W.A. et al, Photodissociation of ligands from heme and heme proteins. Effect of temperature and organic phosphate., J. Biol. Chem. 252, 7955-8 (1977).
Saha, D. C. et al, Comparison of cardiovascular effects of tiletamine-zolazepam, pentobarbital, and ketamine-xylazine in male rats., J. Am. Assoc. Lab. Anim. Sci. 46, 74-80 (2007).
Savolainen, H. et al., Biochemical effects of CO poisoning in rat brain with special reference to blood COHb and cerebral cyt oxidase activity, Neurosci Lett. 19, 319-23 (1980).
Schmidt, M., et al. "Blood oxygenation and decarboxylation determinants during venovenous ECMO for respiratory failure in adults." Intensive care medicine 39.5 (2013): 838-846.
Schneir, A. et al, Carbon monoxide poisoning and pulmonary injury from the mixture of formic and sulfuric acids., Clin Toxicol (Phila) 54, 450-3 (2016).
Shirani, K.Z. et al, The influence of inhalation injury and pneumonia on burn mortality., Ann. Surg. 205, 82-7 (1987).
Sircar, K., et al. (2015). Carbon monoxide poisoning deaths in the United States, 1999 to 2012. The American journal of emergency medicine, 33(9), 1140-1145.
Takeuchi, A. et al, A simple "new" method to accelerate clearance of carbon monoxide., Am J Respir Crit Care Med 161, 1816-9 (2000).
Teerapuncharoen, K., et al. "Successful treatment of severe carbon monoxide poisoning and refractory shock using extracorporeal membrane oxygenation." Respiratory care 60.9 (2015): e155-e160.
Walker, P. F., et al. "Diagnosis and management of inhalation injury: an updated review." Critical Care 19.1 (2015): 1-12.
Wang, G. S., et al. "Extracorporeal membrane oxygenation (ECMO) for severe toxicological exposures: review of the Toxicology Investigators Consortium (ToxIC)." Journal of medical toxicology 12.1 (2016): 95-99.
Weaver, L.K. et al, Carboxyhemoglobin half-life during hyperbaric oxygen in a patient with lung dysfunction: a case report., Undersea Hyperb Med 44, 173-177 (2017).
Weaver, L.K. et al, Carboxyhemoglobin half-life in carbon monoxide-poisoned patients treated with 100% oxygen at atmospheric pressure., Chest 117, 801-8 (2000).
Weaver, L.K. et al, Hyperbaric oxygen for acute carbon monoxide poisoning., N. Engl. J. Med. 347, 1057-67 (2002).
Welch, A. J. et al, Optical-Thermal Response of Laser-Irradiated Tissue (New York: Springer Science and Business Media, LLC, 1995), pp. 1-25.

* cited by examiner

A

B

SYSTEM AND METHOD FOR EXTRACORPOREAL CARBON MONOXIDE REMOVAL WITH PHOTOTHERAPY

CROSS-REFERENCE TO RELATED APPLICATIONS

The present application is a U.S. National Stage of International Application No. PCT/US2019/040656 filed Jul. 3, 2019 which is based on, claims priority to, and incorporates herein by reference in its entirety United States Provisional Patent Application No. 62/693,620, filed Jul. 3, 2018, and entitled "Extracorporeal Carbon Monoxide Removal with Phototherapy".

STATEMENT REGARDING FEDERALLY SPONSORED RESEARCH

Not Applicable.

BACKGROUND

Carbon monoxide (CO) poisoning impairs tissue oxygenation as CO avidly binds to hemoglobin (Hb) to form carboxyhemoglobin (COHb), which cannot transport oxygen. Currently, treatment of CO poisoning involves breathing 100% oxygen to attempt to rapidly remove CO. Hyperbaric oxygen therapy and/or hyperventilation therapy or exercise can further increase the rate of CO elimination but the necessary facilities and equipment may be not be readily available. Visible light is also known to photodissociate CO from Hb, with a single photon dissociating one CO molecule from Hb.

Smyczynski suggested in U.S. Pat. No. 8,858,880 that light radiation at 540 nanometers (nm) and/or 570 nm could be used to treat CO poisoning by photodissociating COHb in blood passing through an extracorporeal gas exchanger. The treatment system of Smyczynski involves removing and recirculating anticoagulated blood from a patient through an extracorporeal oxygenator. The blood passing through the extracorporeal oxygenator is irradiated with light from a laser at either 540 nm and/or 570 nm. The extracorporeal oxygenator is designed such that the blood-light contact surface is as large as possible because the 540 nm and/or 570 nm light does not penetrate deeply into the blood stream before becoming completely absorbed. The 540 nm and 570 nm light wavelengths are chosen by Smyczynski because these wavelengths align with peaks in the COHb absorption spectra.

BRIEF SUMMARY

The present disclosure provides systems and methods for extracorporeal CO removal using phototherapy. In particular, systems and methods are provided for a extracorporeal phototherapy system that emits light onto opposing sides of an oxygenator that includes a plurality of microporous hollow fiber membranes arranged in layers to photodissociate CO from Hb.

In one aspect, the present disclosure provides an extracorporeal phototherapy system for removing carbon monoxide from whole blood. The extracorporeal phototherapy system includes an oxygenator having a plurality of membrane layers each with a plurality of microporous hollow fiber membranes. The plurality of microporous hollow fiber membranes each include an external surface and an internal channel. Each of the plurality of microporous membrane layers is rotationally offset with respect to an adjacent layer. The oxygenator further includes a gas inlet port in fluid communication with a first end of the internal channels, a gas outlet port in fluid communication a second end of the internal channels, a blood inlet port in fluid communication with the external surfaces, and a blood outlet port in fluid communication with the external surfaces. The extracorporeal phototherapy system further includes a light source configured to output light and arranged to emit the light output by the light source onto at least one surface of the oxygenator.

In one aspect, the present disclosure provides an extracorporeal phototherapy system for removing carbon monoxide from whole blood. The extracorporeal phototherapy system includes an oxygenator having a plurality of membrane layers, a gas inlet port configured to provide fluid communication through internal channels formed in each of the plurality of membrane layers and to a gas outlet port, and a blood inlet port configured to provide fluid communication around external surfaces defined by each of the plurality of membrane layers and to a blood outlet port. The extracorporeal phototherapy system further includes a first light source configured to output light and arranged to emit the light output by the first light source onto a first side of the oxygenator, and a second light source configured to output light and arranged to emit the light output by the second light source onto a second side of the oxygenator opposite to the first side.

In one aspect, the present disclosure provides a method of removing carbon monoxide from whole blood. The method includes flowing whole blood over a plurality of microporous hollow fibers arranged within an oxygenator, flowing oxygen through the plurality microporous hollow fibers, and emitting light from a light source onto opposing sides of the plurality of microporous hollow fibers to photodissociate carboxyhemoglobin in the whole blood.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings which may not be drawn to scale.

DETAILED DESCRIPTION

The term "visible light" as used herein refers to a portion of the electromagnetic spectrum, generally bound between wavelengths of approximately 380 nanometers (nm) and approximately 750 nm, that is visible to the human eye. One of skill in the art would recognize that the wavelength range of visible light will vary from person to person depending on one's vision. Thus, the range from 380 nm to 750 nm is a generally accepted range and is not meant to be definitively limiting in any way.

Carbon monoxide intoxication is a leading cause of poisoning related deaths and results in more than 50,000 visits to emergency departments in the United States each year. Exposure to carbon monoxide is often associated with inhalation of other chemicals and particulates, which can damage the airways and alveoli, resulting in acute lung injury and respiratory failure. In soldiers and firefighters, acute respiratory distress syndrome (ARDS) secondary to trauma and burns can be present. Whenever CO poisoning is associated with impaired gas exchange in the lungs, treatment with either normobaric or hyperbaric oxygen might be less effective or noxious.

Figure 1:
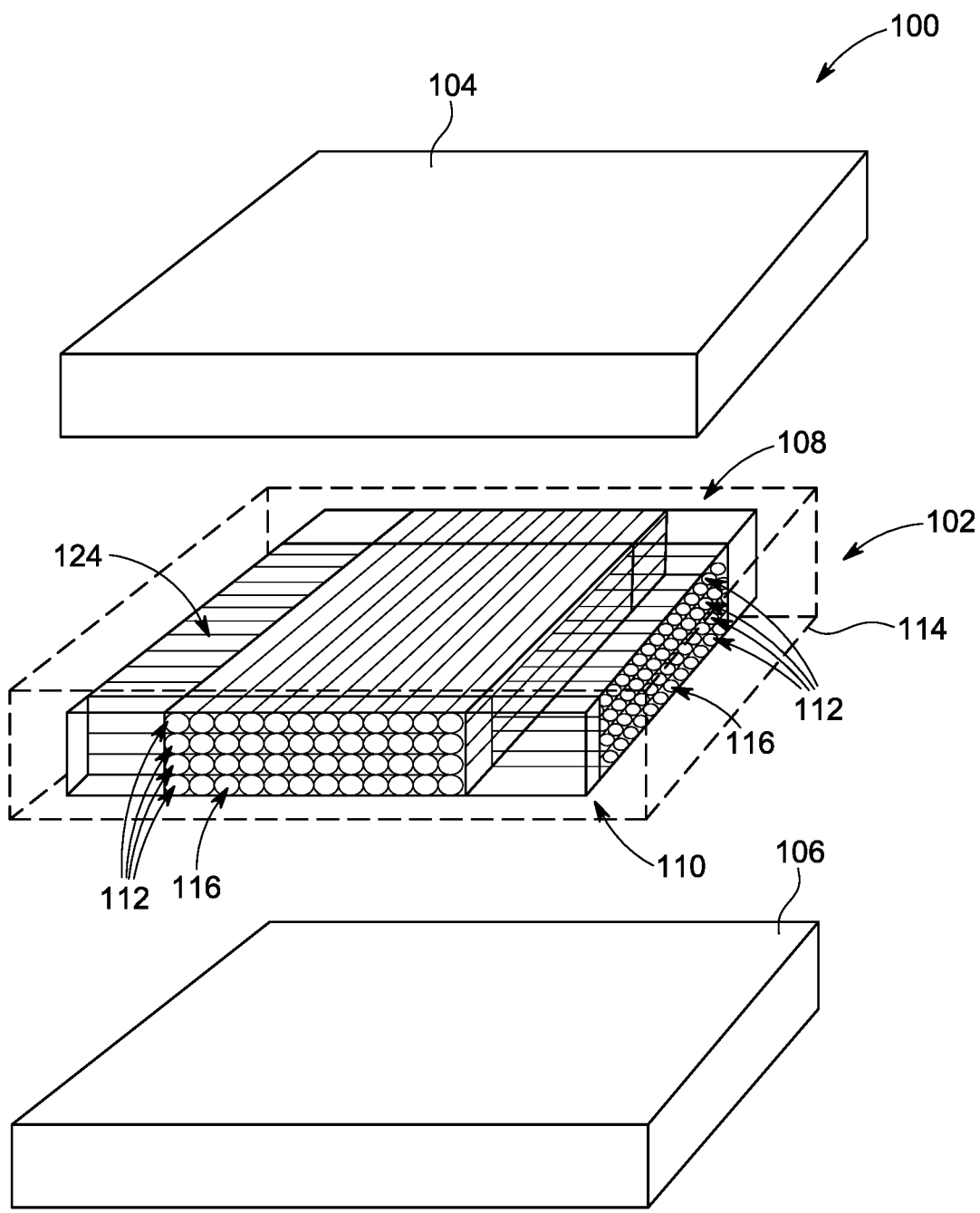
FIG. 1 is a perspective schematic illustration of a extracorporeal phototherapy system according to the present disclosure.
Figure 2:
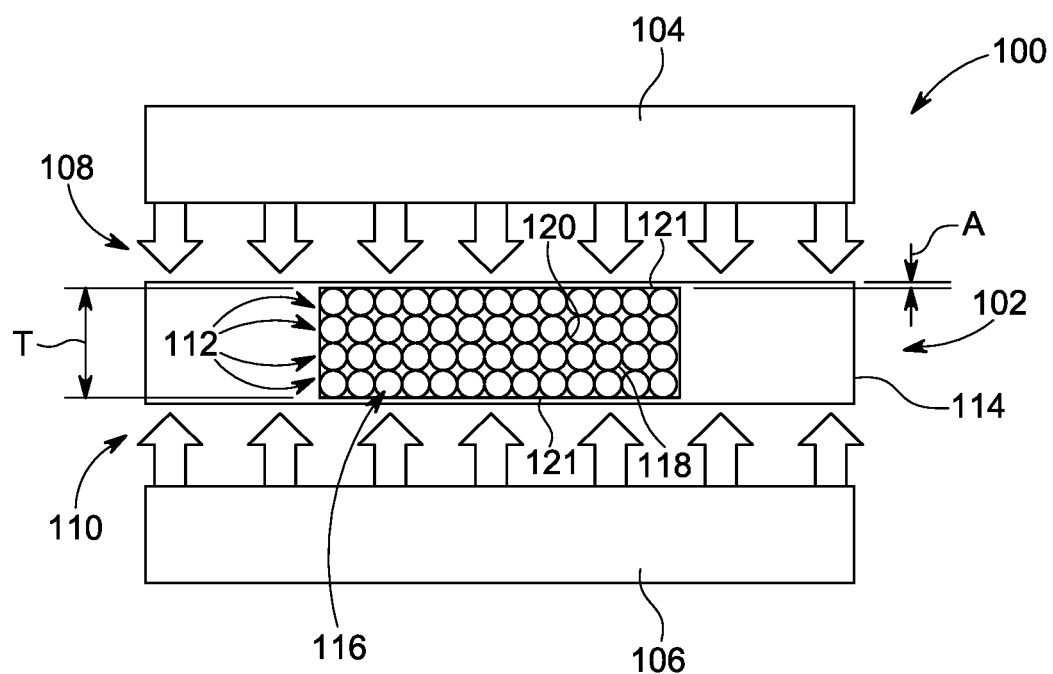
FIG. 2 is a front view of the extracorporeal phototherapy system of FIG. 1.

FIGS. 1 and 2 illustrate one non-limiting example of a extracorporeal phototherapy system 100 according to the present disclosure. In general, the extracorporeal phototherapy system 100 may include at least one light source arranged to emit light at a surface of an oxygenator 102 to promote photodissociation of carboxyhemoglobin (COHb). In the illustrated non-limiting example, the extracorporeal phototherapy system 100 may include a first light source 104 and a second light source 106 arranged on opposing sides of the oxygenator 102. That is, the first light source 104 may be arranged to emit light onto a first side 108 of the oxygenator 102 and the second light source 106 may be arranged to emit light onto a second side 110 of the oxygenator 102.

In some non-limiting examples, the first light source 104 and the second light source 106 may be configured to emit coherent light. In some non-limiting examples, the first light source 104 and the second light source 106 may be configured to emit non-coherent light. In some non-limiting examples, the first light source 104 and the second light source 106 may each be in the form of an array of one or more light emitting diodes (LEDs). In some non-limiting examples, the first light source 104 and the second light source 106 may each be configured to output light at with a wavelength in the visible spectrum. In some non-limiting examples, the first light source 104 and the second light source 106 may each be configured to output light at with a wavelength greater than 600 nanometers (nm). In some non-limiting examples, the first light source 104 and the second light source 106 may each be configured to output light at with a wavelength between than 600 nm and 650 nm.

As described herein, the use of red light (e.g., light with a wavelength generally between 600 nm and 650 nm) may provide increased penetration depth into the oxygenator 102 as well as result in less heating of the blood flowing through the oxygenator 102, when compared to irradiation with light of a lower wavelength (e.g., 450 nm or 532 nm). The increased penetration depth of the red light may provide increased CO elimination from the blood in the oxygenator 102, when compared to irradiation with light of a lower wavelength.

In the illustrated non-limiting example, the oxygenator 102 may include a plurality of membrane layers 112 enclosed within a housing 114. The plurality of membrane layers 112 may each include a plurality of microporous hollow fiber membranes 116 that are arranged in a planar shape and parallel to one another. In general, the plurality of microporous hollow fiber membranes 116 may be fabricated from a material that provides a high diffusion coefficient for CO and oxygen ($O_2$). For example, a silicone material may define a CO diffusion coefficient that is too low to enable effective removal of CO from the treated blood in a single pass. In some non-limiting examples, the plurality of hollow fiber membranes may be fabricated from a microporous polypropylene or a polymethylpentene material, which provide efficient CO removal and oxygenation.

In the illustrated non-limiting example, each of the plurality of membrane layers 112 may be rotationally offset with respect to an adjacent layer. For example, each of the plurality of membrane layers 112 may be rotated ninety degrees with respect to the adjacent layers. In this way, for example, the plurality of microporous hollow fiber membranes 116, which extend generally parallel to one another within a respective one of the plurality of membrane layers 112, may define a generally checkered pattern. That is, one layer of the plurality of microporous hollow fiber membranes 116 may extend in a first direction and an adjacent layer, either above and/or below, may extend in a second direction perpendicular to the first direction.

Each of the plurality of microporous hollow fiber membranes 116 may include an external surface 118 and an internal channel 120. The internal channels 120 may extend axially along each of the plurality of microporous hollow fiber membranes 116. In general, the plurality of microporous hollow fiber membranes 116 may be designed to allow diffusion of $O_2$ and CO between blood flowing over the external surfaces 118 and gas flowing (e.g., $O_2$) through the internal channels 120.

With reference to FIG. 2 in particular, the oxygenator 102 may be designed to provide efficient phototherapy for photodissociation of COHb in CO-poisoned blood (e.g., whole blood). In conventional oxygenators, an air gap may be formed between the first layer of membranes and a treatment surface 121 (e.g., top and bottom surfaces of the oxygenator 102 from the perspective of FIG. 2). During operation, a blood layer may form in this air gap and, since this blood layer is not flowing over a membrane layer, the efficiency of phototherapy to eliminate CO from the blood may be significantly reduced. That is, although the phototherapy may aid in photodissociating COHb, oxygenation and removal of the CO, which are facilitated by the plurality of microporous hollow fiber membranes 116, must be provided to prevent rebinding of the CO to hemoglobin. As such, the oxygenator 102 may be designed to reduce or eliminate an air gap A formed between a treatment surface 121 (i.e., an incident on which the first light source 104 and the second light source 106 emit light) and the layer of the plurality of membrane layers 112 adjacent to the treatment surface 121. The air gap A may be at the top and the bottom. In this way, for example, the oxygenator 102 may ensure that the emitted light is emitted onto blood flowing over one of the plurality of microporous hollow fiber membranes 116.

In some non-limiting examples, to further increase the efficacy of the phototherapy elimination of CO from blood in the oxygenator 102, the oxygenator 102 may be designed with a thickness T that ensures that the light emitted by the first light source 104 and the second light source 106 may penetrate through to all of the plurality of membrane layers 112. In general, a number of layers in the plurality of membrane layers 116 may define the thickness T (e.g., via an outer diameter defined by the external surfaces 118). As such, in some non-limiting examples, the oxygenator 102 may be designed with a predetermined number of layers in the plurality of membrane layers 112 to achieved a desired thickness T. In some non-limiting examples, the thickness T may be less than 15 millimeters (mm). In some non-limiting examples, the thickness T may be less than 10 mm.

Figure 3:
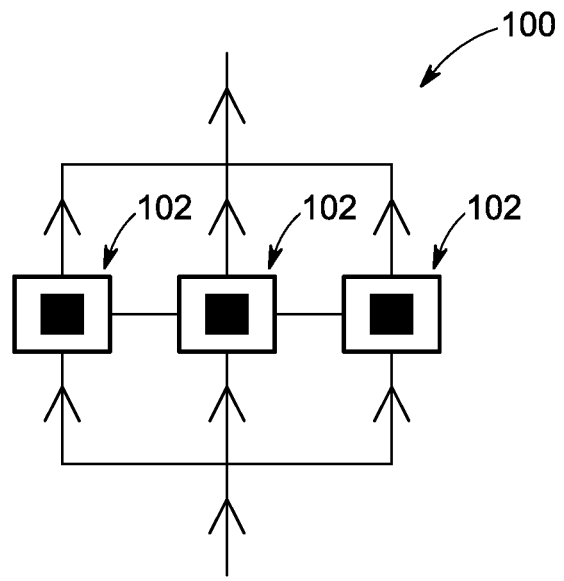
FIG. 3 is a schematic illustration of a parallel porting configuration of the extracorporeal phototherapy system of FIG. 1.
Figure 4:
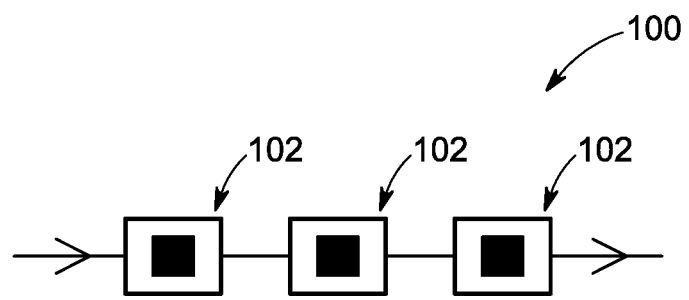
FIG. 4 is a schematic illustration of a series porting configuration of the extracorporeal phototherapy system of FIG. 1.

In general, the oxygenator 102 may be configured to exchange CO and $O_2$ via diffusion through the plurality of microporous hollow fiber membranes 116 in blood flowing over the external surfaces 118. To facilitate blood flow and gas flow through the oxygenator 102, the housing 114 may be provided with one or more ports to facilitate connections to flow devices (e.g., pumps, gas tanks, etc.) arranged externally from the oxygenator 102. Alternatively or additionally, one or more of the oxygenators 102 may be placed in parallel (see, e.g., FIG. 3) or in series (see, e.g., FIG. 4).

Figure 5:
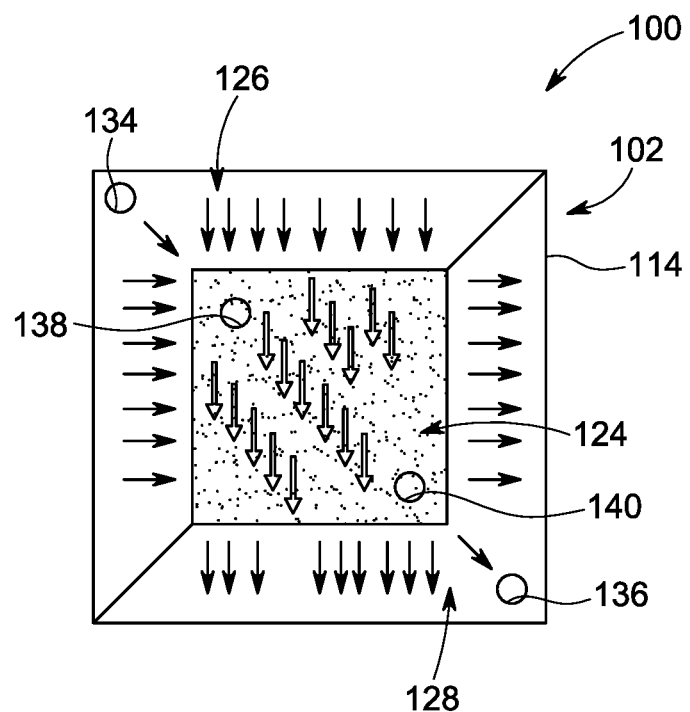
FIG. 5 is a top plan view of the extracorporeal phototherapy system of FIG. 1 illustrating blood and gas ports.

With reference to FIG. 5 in particular, in general, the oxygenator 102 may be separated into a blood compartment 124, a gas inlet compartment 126, and a gas outlet compartment 128. In some non-limiting examples, an adhesive (e.g., a silicone adhesive) may be applied to seal the blood compartment 124 from the gas inlet compartment 126 and the gas outlet compartment 128. The seal between the blood compartment 124 and the gas inlet compartment 126 may allow a first end 130 of the plurality of microporous hollow fiber membranes 116 to protrude into gas inlet compartment 126. The seal between the blood compartment 124 and the gas outlet compartment 128 may allow a second end 132 of the plurality of microporous hollow fiber membranes 116 to protrude into the gas outlet compartment 128. In this way for example, the first ends 130 and the second ends 132 of the plurality of microporous hollow fiber membranes 116 may be sealed from the blood compartment 124 to allow gas flow through the internal channels 120 and prevent blood from flowing into the internal channels 120. A remainder of the plurality of microporous hollow fiber membranes 116 not sealed off by the gas inlet compartment 126 and the gas outlet compartment 128 may be arranged within the blood compartment 124. Thus, the blood compartment 124 may provide a sealed compartment within which blood may flow over the external surfaces 118 of the plurality of microporous hollow fiber membranes 116.

In the illustrated non-limiting example, the housing 114 may include a gas inlet port 134, a gas outlet port 136, a blood inlet port 138, and a blood outlet port 140. The gas inlet port 134 may be arranged within the gas inlet compartment 126 and may be in fluid communication with the first ends 130 of the internal channels 120. The gas outlet port 136 may be arranged within the gas outlet compartment 136 and may be in fluid communication with the second ends 132 of the internal channels 120. The blood inlet port 138 and the blood outlet port 140 may be arranged within the blood outlet compartment 124. In general, an arrangement of the gas inlet port 134, the gas outlet port 136, the blood inlet port 138, and the blood outlet port 140 may provide gas flow and blood flow in a common direction (e.g., diagonal from upper left to lower right from the perspective of FIG. 5). In this way, for example, the oxygenator 102 may aid in preventing or minimizing a rebinding rate of COHb.

In some non-limiting examples, the gas inlet port 134 may be in fluid communication with a fluid source configured to supply gas to the gas inlet port 134 at a predetermined flow rate. In some non-limiting examples, the fluid source may be configured to supply 100% $O_2$ to the gas inlet port 134. Using 95% oxygen and 5% CO2 may be desirable in some settings. If removing CO2 with the extracorporeal device, removal of CO from the lungs will be impaired based on breathing, with a null effect on overall CO removal rate as a result. Providing the device with some CO2 (50%) will not materially affect arterial PCO2, respiratory drive and the like. In some non-limiting examples, the fluid source may be configured to supply air to the gas inlet port 134. In general, the blood inlet port 138 may be in fluid communication with a pump, or another fluid flow device, that is configured to draw whole blood from a patient or a reservoir connected to the patient (e.g., via cannulas inserted into one or more veins of the patient). The whole blood removed from the patient may flow through the oxygenator 102 over the external surfaces 118 of the plurality of microporous hollow fiber membranes 116 to the blood outlet port 140. The blood outlet port 140 may be in fluid communication with the patient (e.g., via one or more cannulas inserted into one or more veins of the patient). As such, the whole blood may be recirculated through the oxygenator 102 and the patient.

In general, the gas flow rate supplied to the gas inlet port 134 may be higher than a blood flow rate supplied to the blood inlet port 138. In some non-limiting examples, a ratio between the gas flow rate supplied to the gas inlet port 134 to the blood flow rate supplied to the blood inlet port 138 may be greater than 5:1. In some non-limiting examples, a ratio between the gas flow rate supplied to the gas inlet port 134 to the blood flow rate supplied to the blood inlet port 138 may be greater than 10:1. If the ratio between GAS and BLOOD flow rates is appreciably elevated, an undesirable air gas embolism can be introduced into blood. Up to 10 times higher gas flow than blood flow can be used as a rule of thumb. For example, 1 L/min blood flow can be used with 10 L/min gas flow, 500 ml/min blood flow can be used with 5 L/min gas flow and the like. Of course, other parameters will work beyond this rule of thumb. In some non-limiting examples, the gas flow rate provided to the gas inlet port 134 may provide a partial pressure of $O_2$ ($PO_2$) between 400 millimeters of mercury (mmHg) and 500 mmHg. The high gas flow rates compared to the blood flow rates aid the oxygenator 102 in reducing COHb rebinding rates and provide needed ventilation to expel photodisassociated CO.

Figure 6:
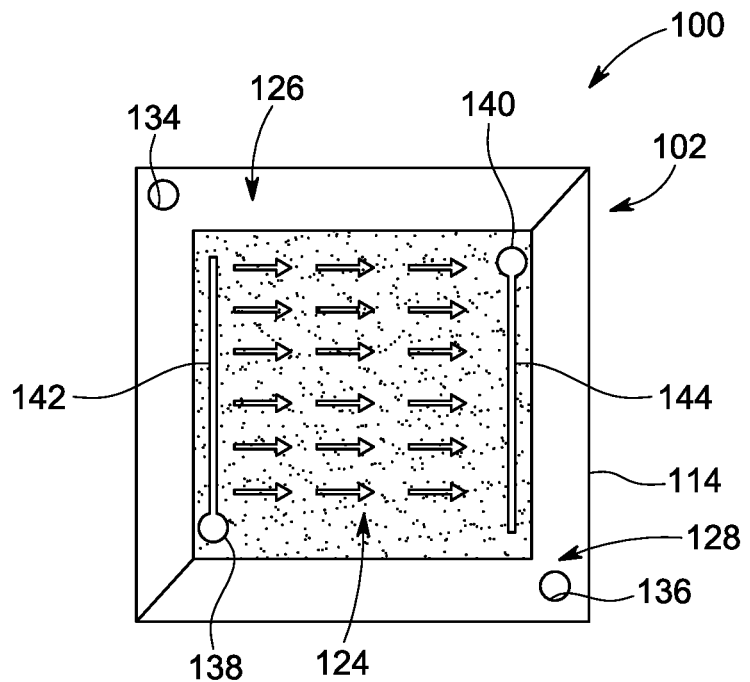
FIG. 6 is a top plan view of the extracorporeal phototherapy system of FIG. 1 illustrating blood ports and channels.

During operation, it is important to design the oxygenator 102 to ensure that blood covers the a substantial portion of the blood compartment surface area. In this way, for example, the surface area for treatment may be expanded to encompass the entire or a substantial portion of the blood compartment 124. FIG. 6 illustrates one non-limiting example where the housing 114 includes an blood inlet channel 142 connected to the blood inlet port 138 and a blood outlet channel 144 connected to the blood outlet port 140. The blood inlet channel 142 extends along one side of the blood compartment 124 and the blood outlet channel 144 extend along an opposite side of the blood compartment 124 in a direction that is general parallel to the blood inlet channel 142. In this way, for example, blood may be distributed from the blood inlet port 138 along one side of the blood compartment 124. With the blood distributed along one side of the blood compartment 124, the blood may flow along the blood compartment 124 to the opposing side and into the blood outlet channel 144. The blood inlet channel 142 and the blood outlet channel 144 may aid in distributing the blood over the entire surface area, or a substantial portion of the surface area, of the blood compartment 124.

Figure 7:
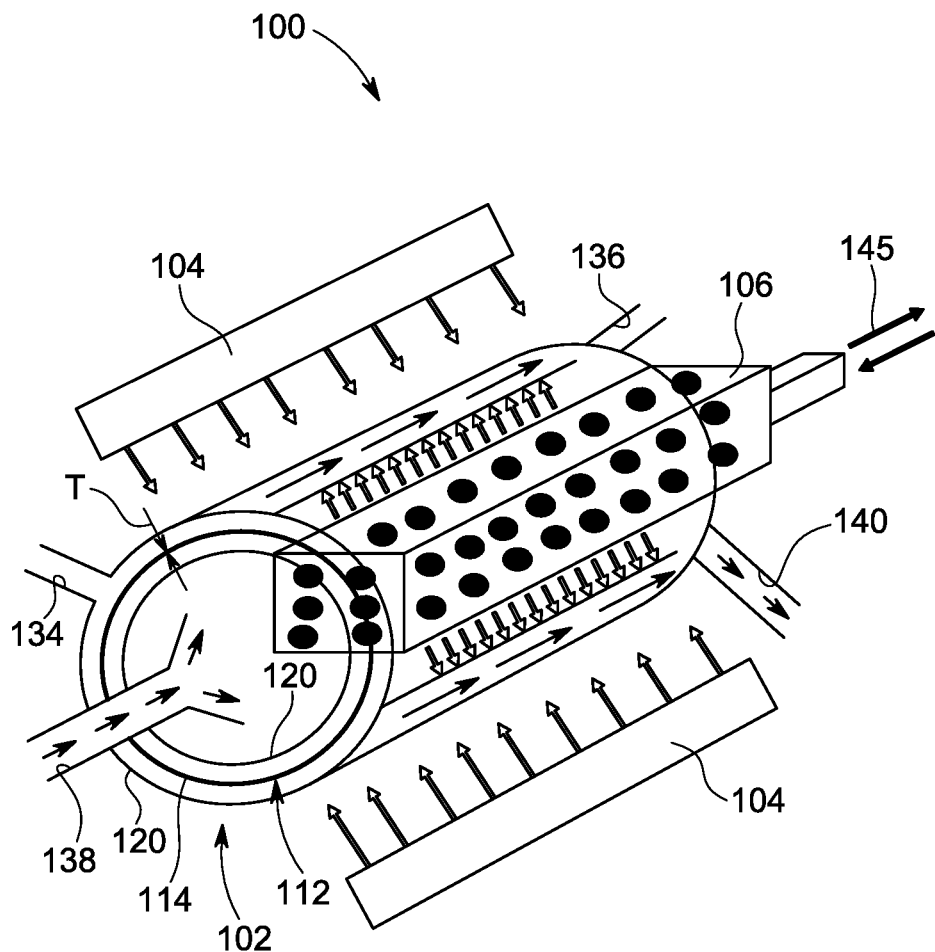
FIG. 7 is a perspective schematic illustration of a cylindrical configuration of an extracorporeal phototherapy system according to the present disclosure.

In the illustrates non-limiting examples of FIGS. 1-6 the oxygenator 102 may define a generally planar shape (e.g., a thin rectangular prism). In other non-limiting examples, the oxygenator 102 may be designed in alternative shapes while maintaining the principles and characteristics described herein. FIG. 7 illustrates one non-limiting example of the extracorporeal phototherapy system 100 where the oxygenator 102 defines a generally cylindrical shape. Similar to the planar design of the oxygenator 102, the cylindrical design of the oxygenator 102 may enable phototherapy to be applied onto two opposing surfaces of the oxygenator 102. In the illustrated non-limiting example, the first light source 104 may define a generally annular shape that extends concentrically around an outer surface of the oxygenator 102. The second light source 106 may be define a generally rectangular prism shape and may be arranged within an internal surface of the oxygenator 102. In other non-limiting examples, the second light source 106 may define alternative shapes (e.g., cylindrical).

In the illustrated non-limiting example, a flow of cooling fluid 145 (e.g., water) may be provided to the second light source 106 arranged within the oxygenator 102. In this way, for example, cooling may be provided to the blood flowing through the oxygenator 102. The cooling system may be a heat exchanger with cold water that cools entering inlet blood a few degrees Celcius.

Figure 8:
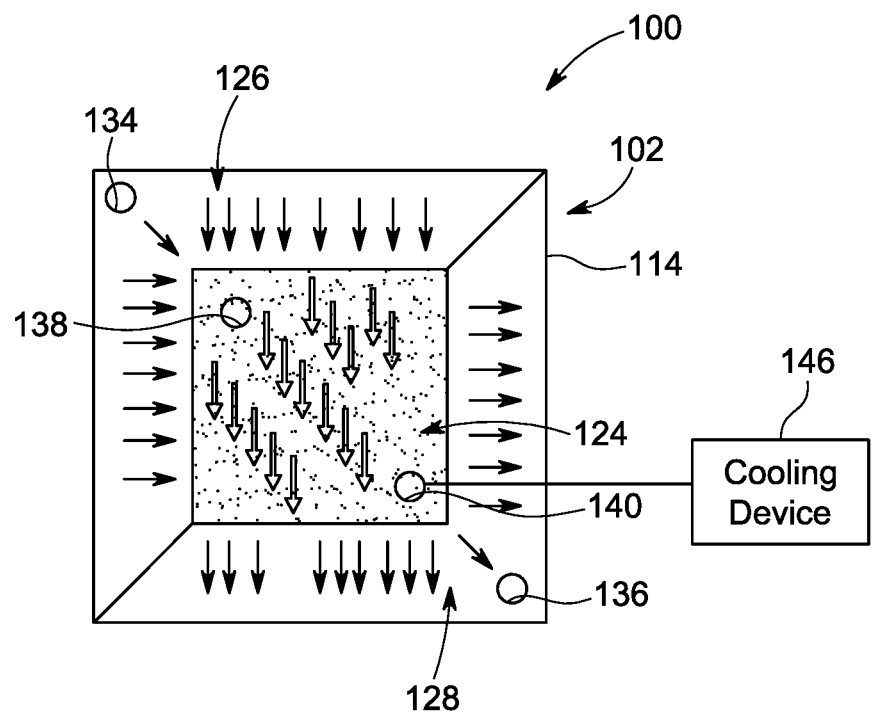
FIG. 8 is a top plan view of the extracorporeal phototherapy system of FIG. 1 illustrating a cooling device connected to the blood outlet port.
Figure 9:
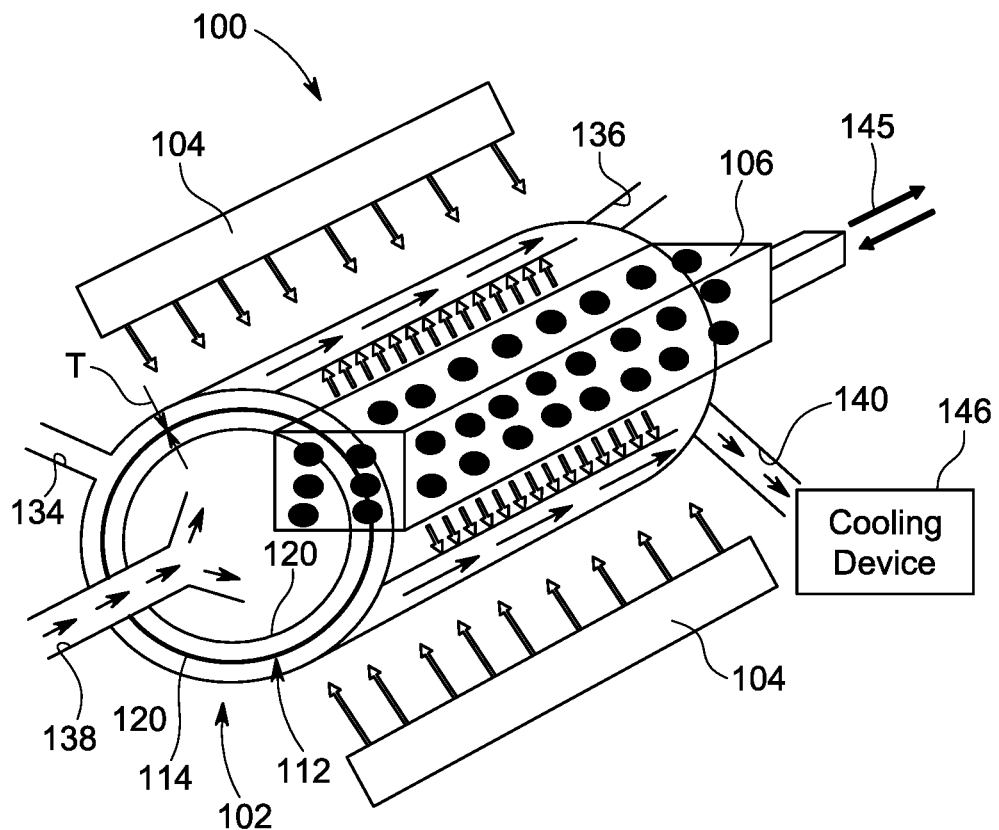
FIG. 9 is a perspective schematic illustration of the cylindrical configuration of the extracorporeal phototherapy system of FIG. 7 illustrating a cooling device connected to the blood outlet port.

In some non-limiting examples, as illustrated in FIGS. 8 and 9, a cooling device 146 (e.g., a heat exchanger, a photoelectric cooler, an evaporative cooler, etc.) may be placed in fluid communication with the blood outlet port 140 to selectively provide cooling to the blood flow leaving the oxygenator 102 and flowing toward, for example, a patient. The cooling device 146 may be configured to cool the blood flowing from the blood outlet port 140 to a predetermined temperature (e.g., around body temperature). In some non-limiting examples, the cooling device 146 may be in communication with a controller that is configured to monitor an outlet temperature of the blood flowing from the blood outlet port 140 and control the cooling device 146 to maintain the blood temperature flowing from the cooling device 146 to the predetermined temperature.

One non-limiting example of operation of the extracorporeal phototherapy system 100 will be described with reference to FIGS. 1-9. In general, the extracorporeal phototherapy system 100 may provide removal of CO from blood in a patient having CO poisoning. For example, the extracorporeal phototherapy system 100 may provide sufficient removal of CO to allow the treatment of CO poisoning in environments where medical care is not easily accessible and breathing $O_2$ is not helping treat the CO poisoning. Typically, to treat a patient having CO poisoning the blood inlet port 138 may be connected to a pump, which is configured to remove whole blood from a patient, and the blood outlet port 140 may be connected to the patient (e.g., via a cannula inserted into a vein of the patient). The gas inlet port 134 may be connected to a gas supply configured to flow, for example, 100% $O_2$ through the internal channels 120 of the plurality of microporous hollow fiber membranes 116 to the gas outlet port 136.

With the gas and blood flows connected the oxygenator 102, the flow of whole blood and oxygen may begin, for example, with the gas flow rate being approximately 5 times greater than or equal to the blood flow rate, or approximately 10 times greater than or equal to the blood flow rate. While the blood and gas are flowing through the oxygenator 102, the first light source 104 and the second light source 106 may emit light onto opposing sides of the oxygenator 102, specifically, onto treatment surfaces 120 arranged on opposing sides of the blood compartment 124. The light emitted by the first light source 104 and the second light source 106 may penetrate through the plurality of membrane layers 112, for example, due to the thickness T defined by the plurality of membrane layers 112 and the penetration capabilities of the light emitted by the first light source 104 and the second light source 106. The photons emitted by the first light source 104 and the second light source 106 may be absorbed by COHb in the blood and photodisassociate the COHb into CO and Hb. The first light source 104 and/or the second light source 106 may be arranged inside of or outside of the oxygenator and/or can also be located on a cooling device 146.

Since the partial pressure of oxygen flowing through the internal channels 120 of the plurality of microporous hollow fiber membranes 116 is much greater than in the blood flowing over the external surfaces 118, oxygen may diffuse through the plurality of microporous hollow fiber membranes 116 to bind to deoxygenated Hb. The CO may diffuse into the plurality of microporous hollow fiber membranes 116 and the gas flow may expel the CO from the oxygenator 102. As such, the design and properties of the extracorporeal phototherapy system 100 may facilitate efficient and effective removal of CO from whole blood in a patient having CO poisoning.

Of note the average human or rat has a blood volume of 6-8% of body weight or for a 75 kg human that is about 5 liters total blood volume. To clean out most of the CO and replace with O2, one must treat 5L to remove 100% of the CO. As a non-limiting example, if one can process vein-to-vein blood extracorporeally at 250 ml/min to remove 90% of CO on a single phototherapy pass, a liter can be processed every 4 minutes.

EXAMPLES

The following examples set forth, in detail, ways in which the extracorporeal phototherapy systems described herein may be used or implemented, and will enable one of skill in the art to more readily understand the principles thereof. The following examples are presented by way of illustration and are not meant to be limiting in any way.

Development of an Extracorporeal Oxygenator for Phototherapy

A membrane oxygenator was built with a configuration suitable for blood phototherapy and tested the device in an in vitro model of veno-venous extracorporeal blood circulation. The in vitro circuit for blood circulation consisted of an open reservoir (10 ml syringe), a roller pump (NE-9000-G, Farmingdale, N.Y.), silicone tubing and a membrane oxygenator. Blood entering and exiting the CO photo-remover was collected while the CO photo-remover was perfused with de-oxygenated blood and ventilated with 100% oxygen at 1 L/min. For each pair of samples, the actual oxygen transfer and the maximum oxygen transfer were calculated as following:

Actual $O_2$ transfer (ml/min/m2)=$[C_{post}O_2$ (ml/dL)−$C_{pre}O_2$ (ml/dL)]*BF(ml/min/m$^2$);

Maximum $O_2$ transfer (ml/min/m2)=[CmaxO2 (ml/dL)−CpreO2 (ml/dL)]*BF(ml/min/m2), Where:

$C_{pre}O_2$ (ml/dL)=[Hb (g/dL)*$Sat_{pre}O_2$(%)*1.36(ml/g)/100]+[$P_{pre}O_2$(mmHg)*0.003];

$C_{post}O_2$ (ml/dL)=[Hb (g/dL)*$Sat_{post}O_2$(%)*1.36(ml/g)/100]+[$P_{post}O_2$(mmHg)*0.003];

$C_{max}O_2$ (ml/dL)={Hb (g/dL)*[100−COHb(%)−MetHb(%)]*1.36(ml/g)/100}+{[760-47-$P_{post}$CO2](mmHg)*0.003}; and BF (ml/min/m2)=blood flow (ml/min)/gas exchange surface area (m$^2$).

In all equations 'C' refers to content of oxygen in blood, 'pre' refers to blood entering the oxygenator and 'post' refers to blood exiting the oxygenator.

Figure 10:
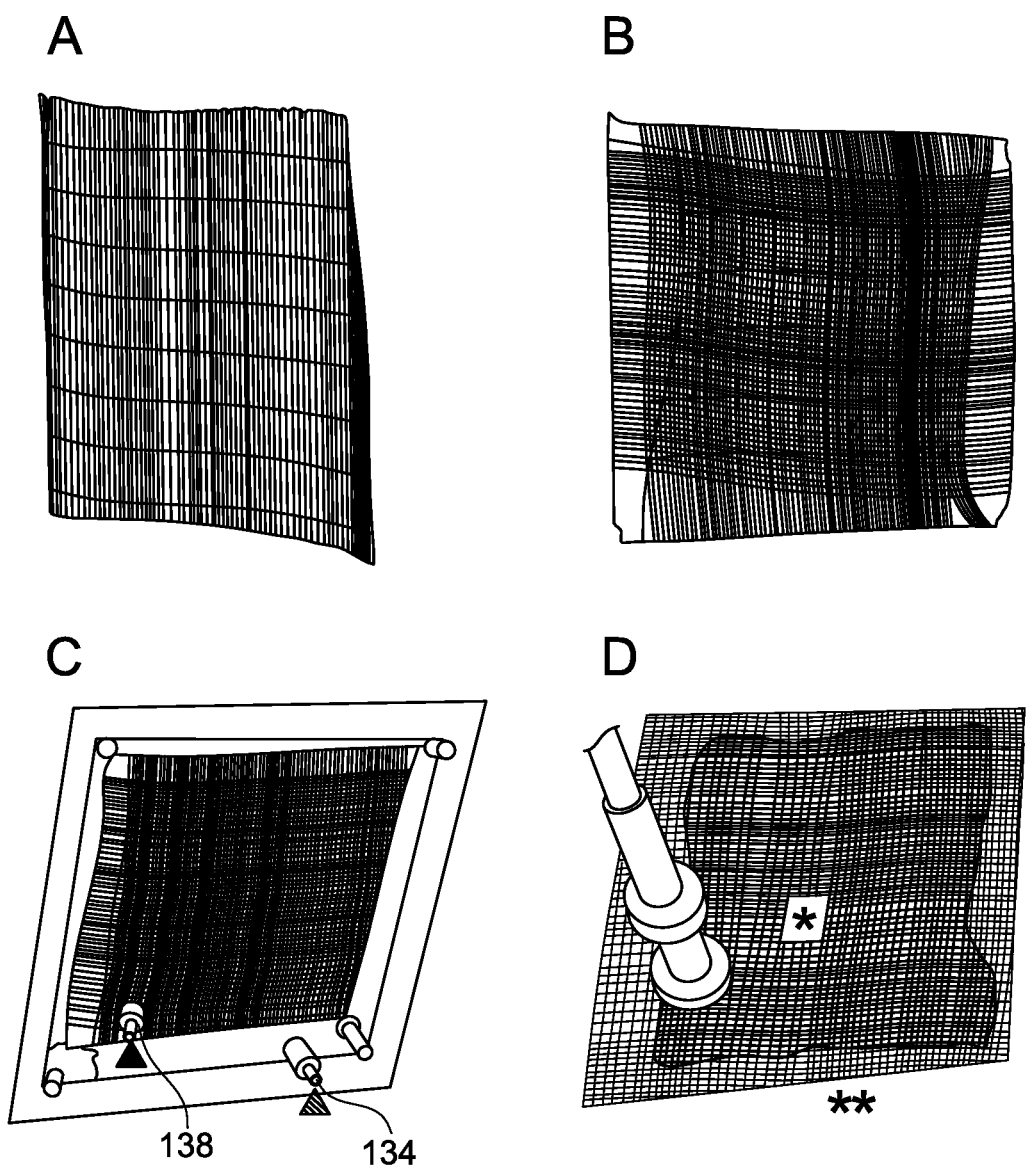
FIG. 10A is a top view of one layer of microporous hollow fiber membranes obtained from a cardiopulmonary bypass oxygenator.
FIG. 10B is a top view of multiple layers of microporous hollow fiber membranes being rotationally offset from each other.
FIG. 10C is a top view of the multiple layers of FIG. 10B sealed in a plexiglass housing having ports for gas and blood flow.
FIG. 10D is a top view of the multiple layers sealed in the housing of FIG. 10C illustrating two sealed compartments formed for blood flow and gas flow.

To create a membrane oxygenator (CO photo-remover) with optimal characteristics for both oxygen transfer, CO removal and venous blood light exposure, a microporous polypropylene membrane for gas exchange was enclosed within and a clear plexiglass case to allow light penetration. The polypropylene membrane was obtained from a disassembled cardiopulmonary bypass oxygenator and cut into 7×7 cm sections as shown in FIG. 10A. Eight sections were placed on top of each other, with each layer rotated 90 degrees relative to the one below as shown in FIG. 10B. The edges of the membranes were sealed with silicone rubber adhesive and enclosed in a clear plexiglass case with ports formed therein to provide a blood inlet 138, a blood outlet (not shown), a gas inlet 134, and a gas outlet (not shown) as shown in FIG. 10C. The configuration of the device was such that two sealed compartments were obtained: a compartment for blood flowing around the hollow fibers, and a compartment for oxygen flowing into the hollow fibers as shown in FIG. 10D. The size of the chamber containing the hollow fibers and the blood was 6 centimeters (cm) wide, 6 cm long, and 4 mm in height. Within the chamber, the priming volume for blood was 4 ml, while the remaining volume was occupied by the hollow fibers. The surface area for gas exchange was 0.05 m$^2$ and the total surface area for phototherapy was 72 cm$^2$.

Figure 11:
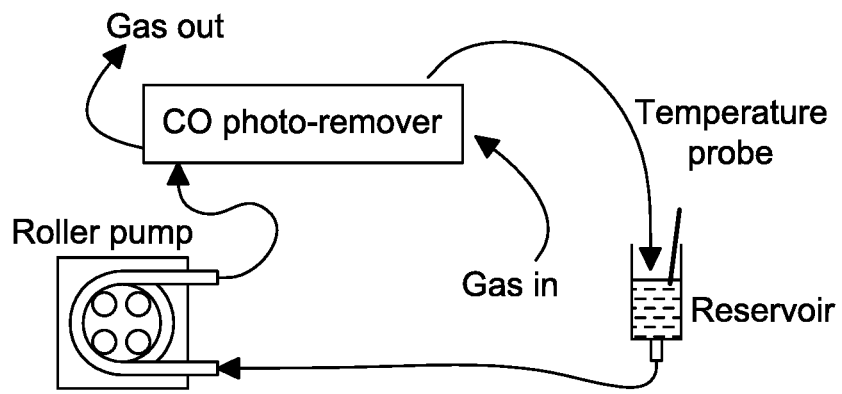
FIG. 11A is a schematic illustration of a test setup used to test a developed extracorporeal phototherapy system using human blood.
FIG. 11B is a schematic illustration of a test setup used to test a developed extracorporeal phototherapy system in a rat study.
Figure 11:
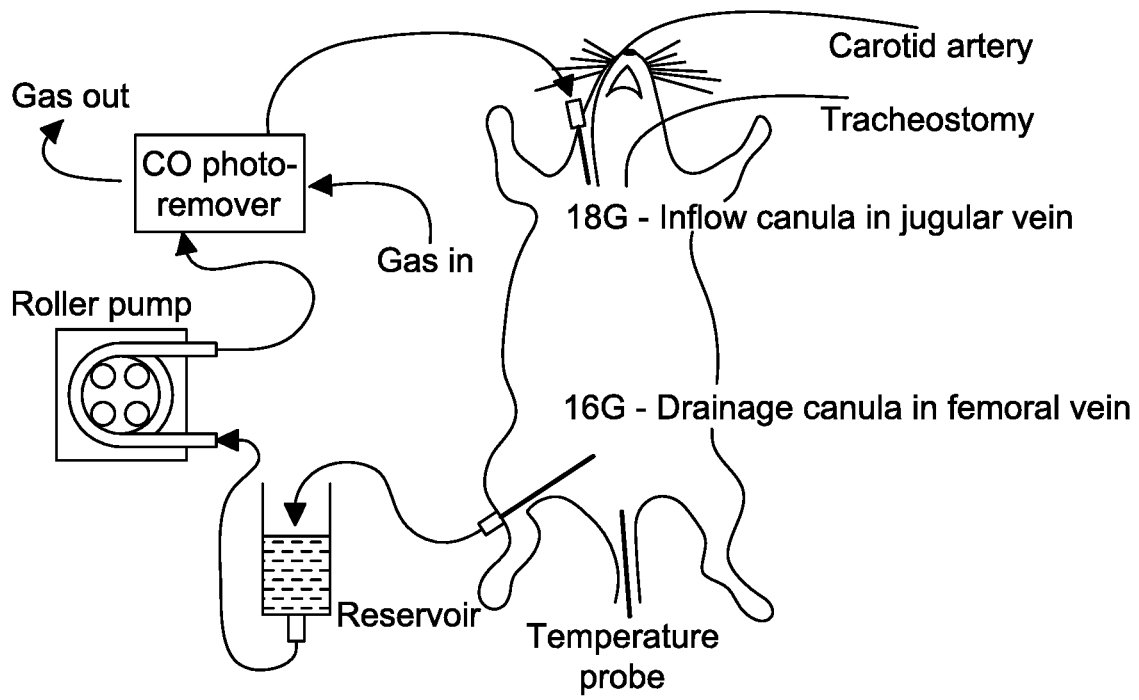
Figure 12:
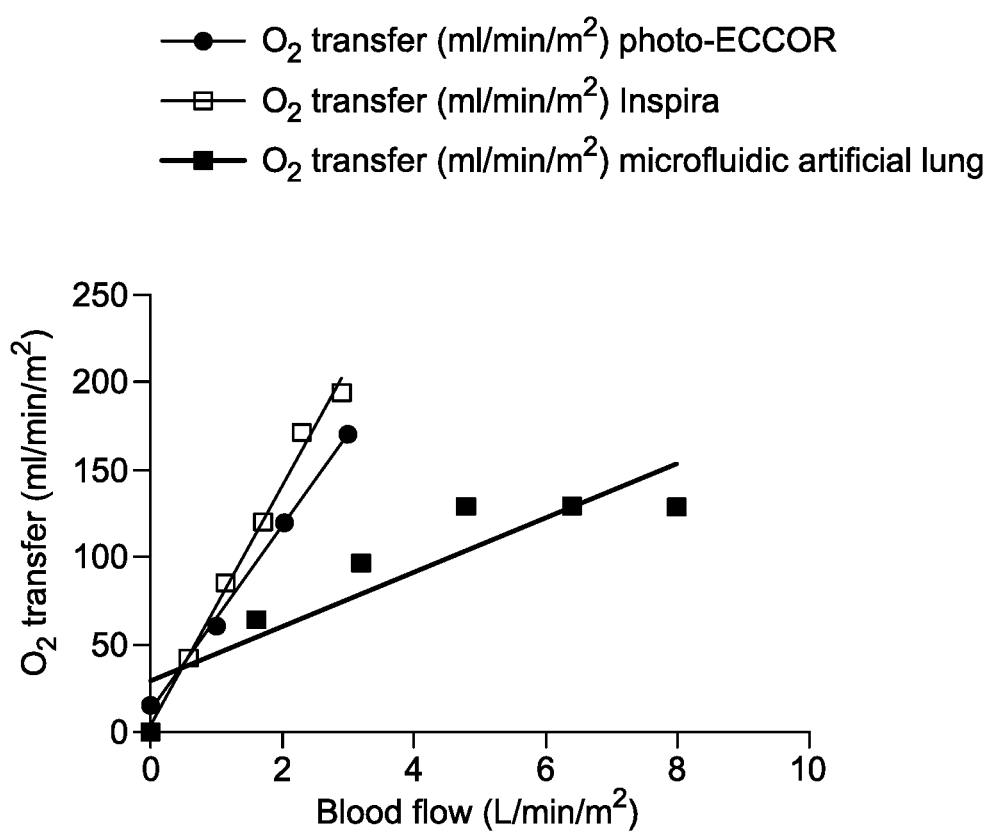
FIG. 12 is a graph illustrating oxygen transfer as a function of blood flow for three different oxygenator devices including a developed oxygenator (photo-ECCOR).
Figure 13:
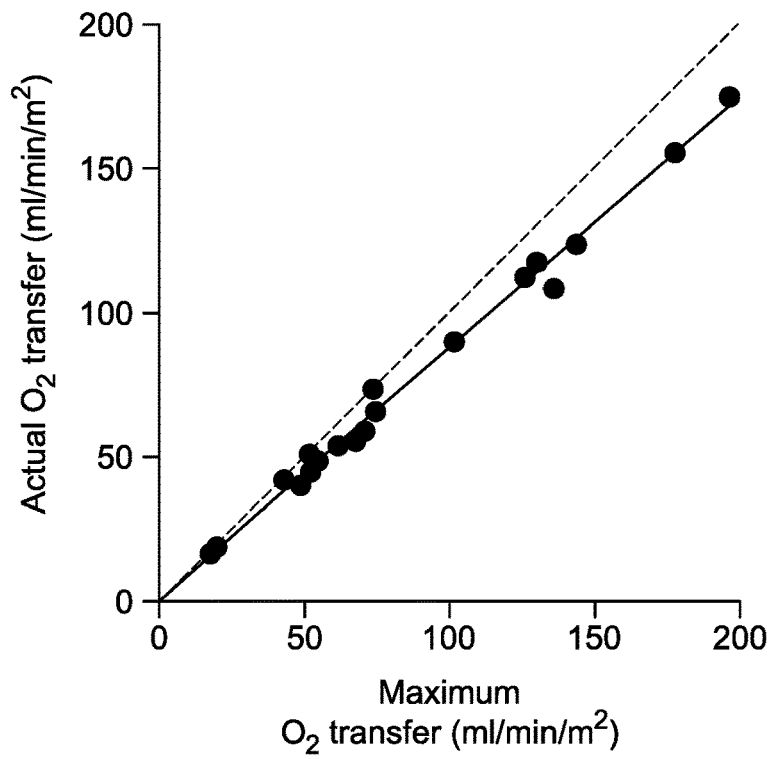
FIG. 13A is a graph illustrating actual oxygen transfer as a function of maximum oxygen transfer for a tested extracorporeal phototherapy system with human blood.
FIG. 13B is a graph illustrating oxygen transfer as a function of blood flow for the tested extracorporeal phototherapy system with human blood.
FIG. 13C is a graph illustrating COHb half-life for a tested extracorporeal phototherapy system on human blood with no phototherapy, blue phototherapy, green phototherapy, and red phototherapy on human blood.
FIG. 13D is a graph illustrating eliminated carbon monoxide as a function of time for the tested extracorporeal phototherapy system on human blood with no phototherapy, blue phototherapy, green phototherapy, and red phototherapy.
Figure 13:
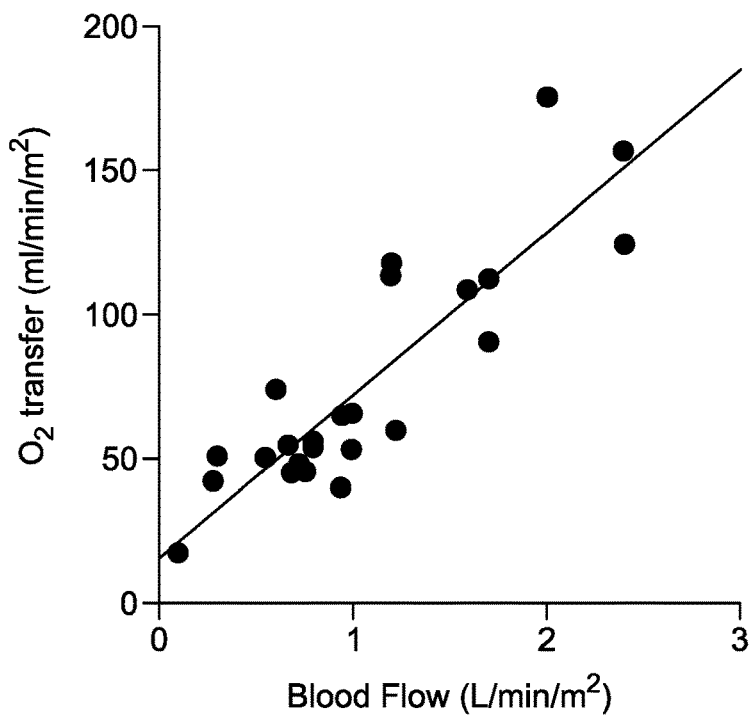
Figure 13:
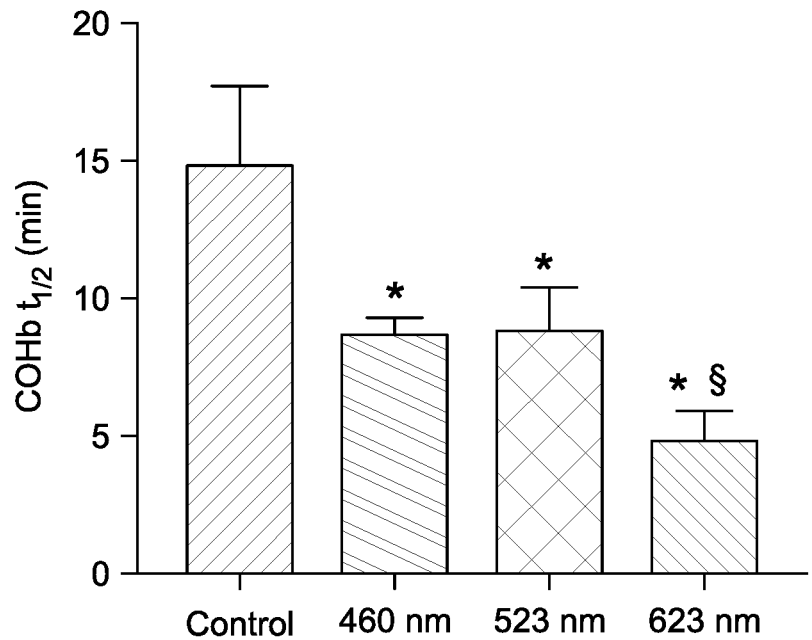
Figure 13:
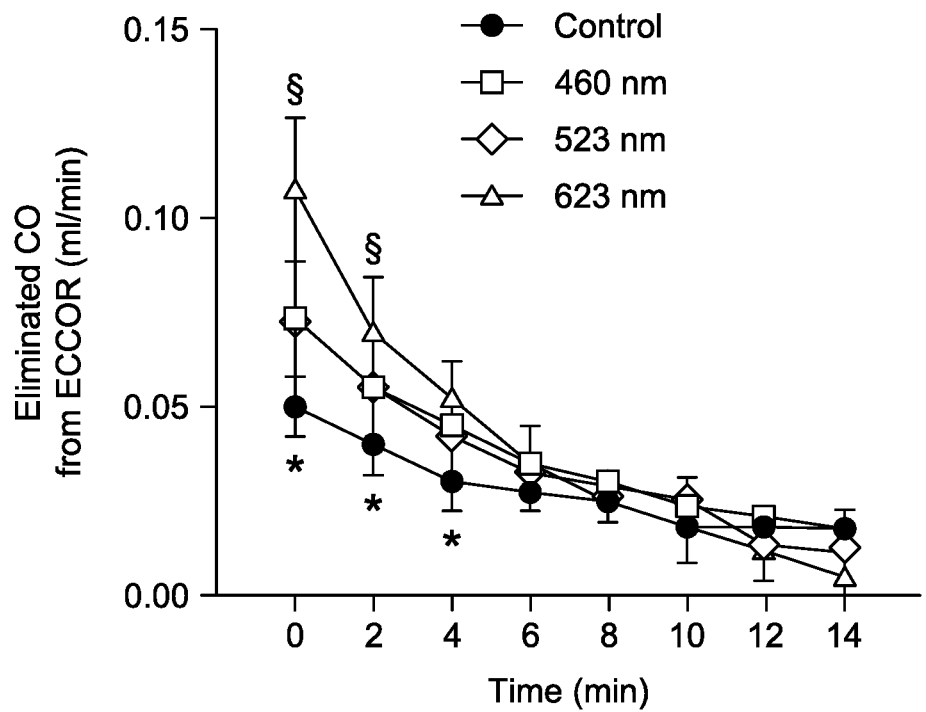

To determine the in vitro oxygenating performance of the CO photo-remover, de-oxygenated whole blood was circulated through the CO photo-remover at various flow rates while the device was "ventilated" with 100% oxygen (see FIG. 11A). In commercially available extracorporeal membrane oxygenation devices, the partial pressure of oxygen in blood ($PO_2$) exiting the membrane lung is between 400 and 500 mmHg (see, e.g., FIG. 12). The $PO_2$ of the blood entering and exiting the CO photo-remover was 35.5±11.9 and 482±72 mmHg, respectively. The actual oxygen transfer was similar to the maximum oxygen transfer ($R2=0.99$, Slope=0.86, $P<0.0001$, see FIG. 13A) and the oxygen transfer increased linearly with increasing blood flow rate ($R2=0.78$, $P<0.0001$, see FIG. 13B). These results indicate that the CO photo-remover has an oxygen transfer performance equivalent to a commercial device used for cardiopulmonary bypass and extracorporeal membrane oxygenation.

Figure 14:
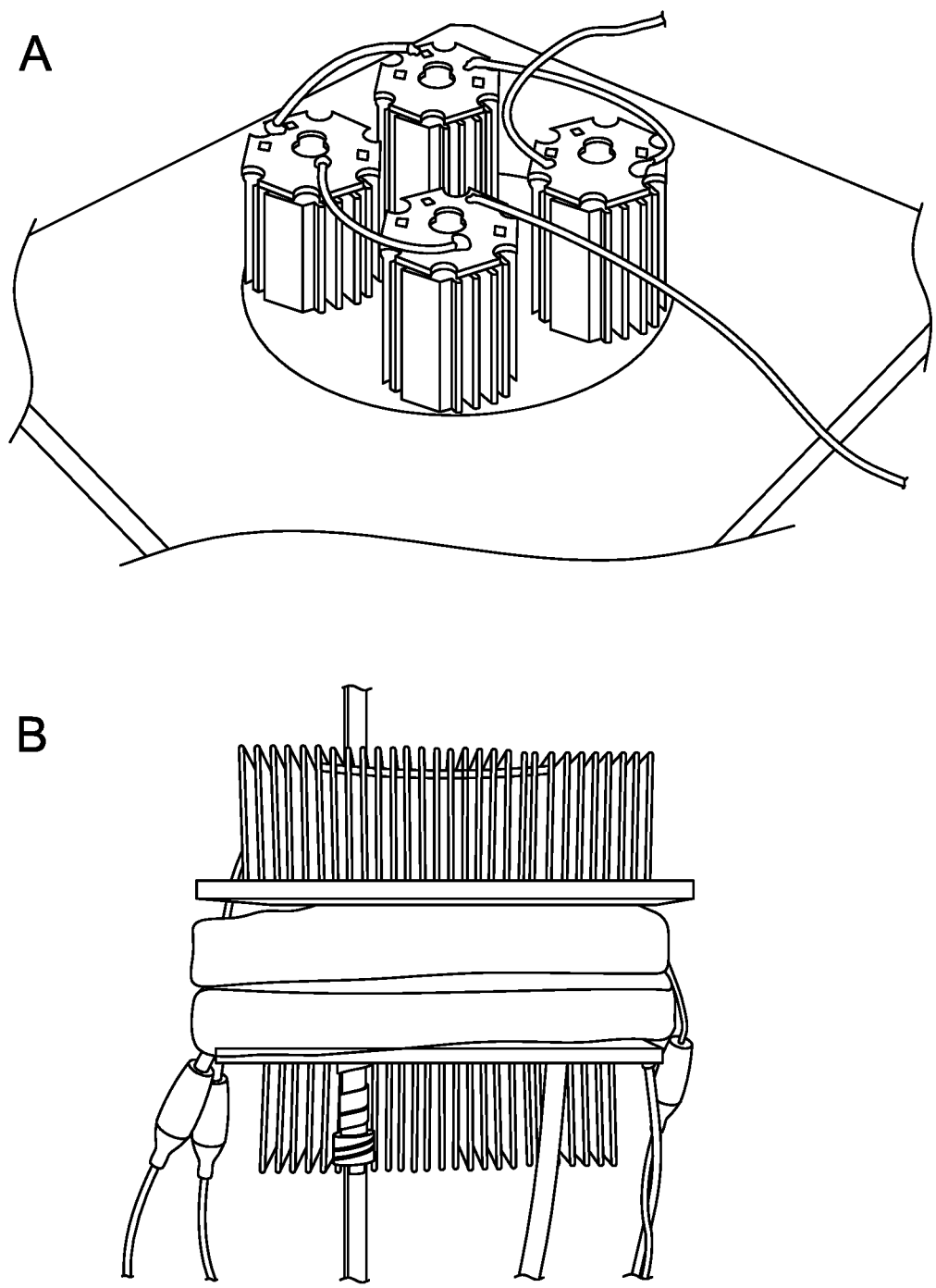
FIG. 14A is a perspective view of a developed light source including four light emitting diodes used in the testing of the extracorporeal phototherapy system.
FIG. 14B is a front view of the develop light source of FIG. 14A with heat sinks installed on opposing sides of an oxygenator.

To test whether the newly developed CO photo-remover was an effective approach to treating CO poisoned blood in vitro, human blood was circulated through the device using a roller pump while the membranes were ventilated with 2% CO in nitrogen. After 10-15 minutes, 80-90% of hemoglobin was saturated with CO. The CO photo-remover was then ventilated with 100% oxygen at 100 ml/min and was exposed to LEDs generated blue (460 nm), green (523 nm), red (623 nm) or no light. The developed light sources are shown in FIGS. 14A and 14B. Light emitting diodes (LEDs, Mouser Electronics, Mansfield, Tex.), with a maximum power of 750 mW, were used to produce green (523 nm), red (623 nm) or blue (460 nm) light. During ECCOR with phototherapy (ECCOR-P), the CO photo-remover was irradiated using a total of 8 LEDs, four on each side of the membrane oxygenator. The irradiance of phototherapy (the light power over the surface area of exposure) was approximately 80 mW/cm$^2$. LEDs were attached to heat sinks, which were ventilated with small fans to dissipate the heat produced during phototherapy (see, e.g., FIG. 14B).

Serial samples of blood were collected to measure COHb and to calculate COHb half-life (COHb-$tv_{1/2}$), while CO concentration exiting the CO photo-remover was measured continuously. During circulation of CO poisoned blood through the CO photo-remover, while the device was ventilated with 100% oxygen but was not treated with phototherapy (control), the COHb-$t_{1/2}$ was 14.9±2.8 min. Compared to control (no exposure to light), addition of either blue or green light reduced COHb-$t_{1/2}$ by approximately 42% (to 8.7±0.6 min and 8.8±1.6 min for blue or green light, respectively, each with $p<0.0001$ compared to control, see FIG. 13C). Exposure of the device to red light reduced COHb-$t_{1/2}$ to 4.9±1.0 min, reflecting a 67% reduction compared to no light ($p<0.0001$) and 44% reduction compared to blue or green light ($p<0.01$ for each comparison). The CO exiting the photo-remover during phototherapy with light (and exposure to 100% oxygen) was greater than during treatment with 100% oxygen alone. Exposure of the CO photo-remover to red light resulted in greater CO elimination than blue or green phototherapy (see FIG. 13D). These results show that phototherapy increases the rate of CO elimination from blood in vitro and that red light is more effective than blue or green light at enhancing the rate of CO removal.

Rat Study

All animal experiments were approved by the Subcommittee on Research Animal Care of the Massachusetts General Hospital, Boston, Mass. Anesthetized and mechanically ventilated Sprague Dawley rats weighing 400-500 g were tested. Rats were anesthetized with Isoflurane 5% in oxygen for 3-5 minutes in a plexiglass chamber. Following a tracheostomy, rocuronium (1 mg·kg$^{-1}$) was injected (i.p.) to induce muscle relaxation and rats were mechanically ventilated (Inspira; Harvard Apparatus, Holliston, Mass). Volume-controlled ventilation was provided at a respiratory rate of 40 breaths·min$^{-1}$, a tidal volume of 10 mL·kg$^{-1}$, positive end expiratory pressure (PEEP) of 2 cmH$_2$O. Anesthesia was maintained with 1-2% isoflurane and continuous muscle relaxation was provided with rocuronium (2-4 mg·kg$^{-1}$·h$^{-1}$). Airway pressure was continuously monitored, as well as end tidal CO$_2$ (ETCO$_2$) which was measured by a capnometer (PhysioSuite, CapnoScan End-Tidal CO$_2$ Monitor, Kent Scientific, Torrington, Conn).

The right carotid artery was cannulated with a PE20 catheter for blood sampling and arterial blood pressure monitoring. A bolus of heparin (200 UI·kg$^{-1}$) and subsequent continuous infusion at 100 UI·kg$^{-1}$·h$^{-1}$ was administered for blood anticoagulation. A custom-made 4-hole, 16-gauge cannula was placed in the right femoral vein and a 18-gauge cannula (Introcan Safety, B Brown Medical Inc., Irvine, Calif.) was placed in the right jugular vein. Fluid resuscitation was maintained infusing 0.9% Saline at a rate of 8 to 12 mL·kg$^{-1}$·h$^{-1}$.

To determine whether the CO photo-remover was able to increase the rate of CO elimination from blood in vivo, the device was tested in a rat model of CO poisoning (see FIG. 11B). Anesthetized and mechanically ventilated rats were poisoned by breathing 2000 ppm CO in air for 30 min. All animals underwent veno-venous extracorporeal blood circulation with blood flow rate ranging from 50 to 100 ml/kg/min (which corresponds to approximately 15-30% of the rat's cardiac output) and were treated by breathing 100% oxygen while the CO photo-remover was provided with: 1) neither gas nor light (control); 2) gas flow (95% O$_2$ and 5% CO$_2$) but no phototherapy (ECCOR); 3) gas flow and phototherapy with combined green and blue light (ECCOR-P-Green/Blue); 4) gas flow and phototherapy with red light (ECCOR-P-Red).

Figure 15:
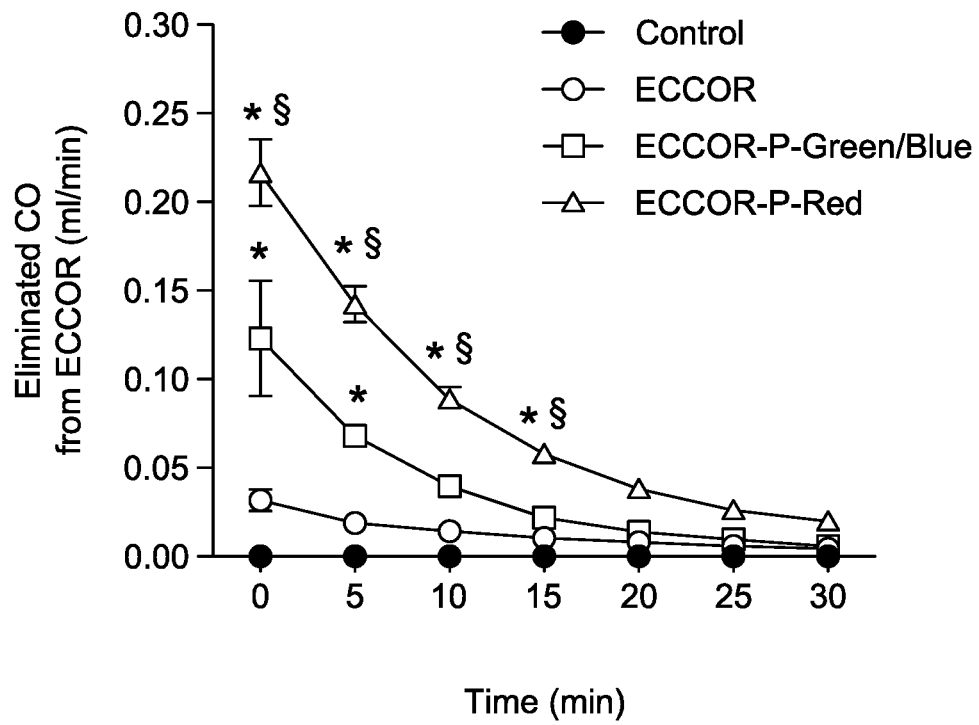
FIG. 15A is a graph illustrating eliminated carbon monoxide as a function of time on carbon-monoxide-poisoned rats with no phototherapy, extracorporeal oxygenation, extracorporeal phototherapy with green/blue light, and extracorporeal phototherapy with red light.
FIG. 15B is a graph illustrating exhaled carbon monoxide as a function of time on carbon-monoxide-poisoned rats with no phototherapy, extracorporeal oxygenation, extracorporeal phototherapy with green/blue light, and extracorporeal phototherapy with red light.
FIG. 15C is a graph illustrating COHb percentage as a function of time on carbon-monoxide-poisoned rats with no phototherapy, extracorporeal oxygenation, extracorporeal phototherapy with green/blue light, and extracorporeal phototherapy with red light.
FIG. 15D is a graph illustrating COHb half-life on carbon-monoxide-poisoned rats with no phototherapy, extracorporeal oxygenation, extracorporeal phototherapy with green/blue light, and extracorporeal phototherapy with red light.
Figure 15:
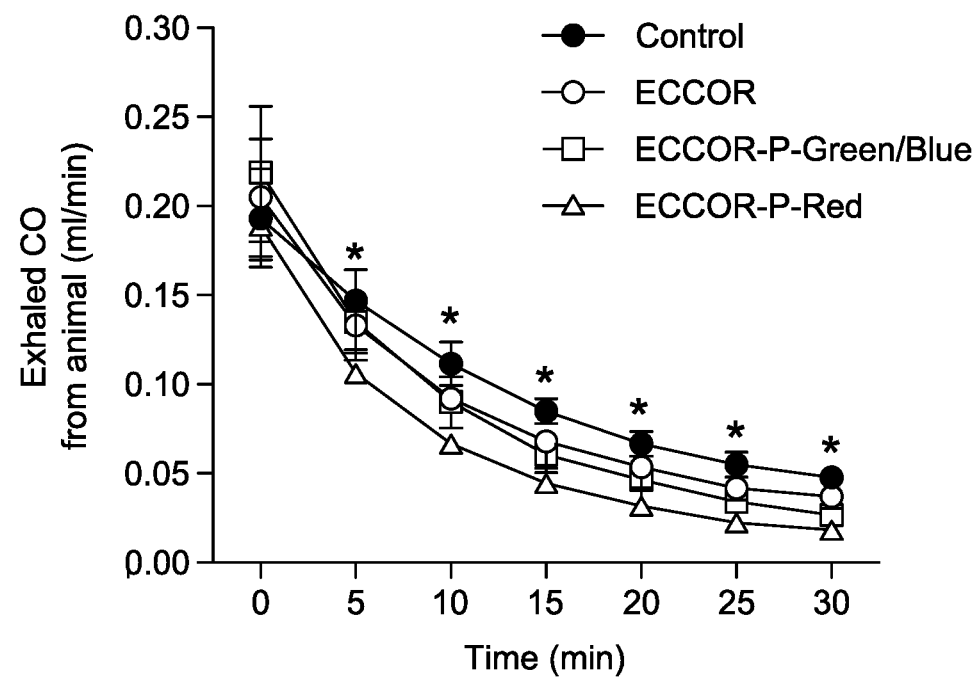
Figure 15:
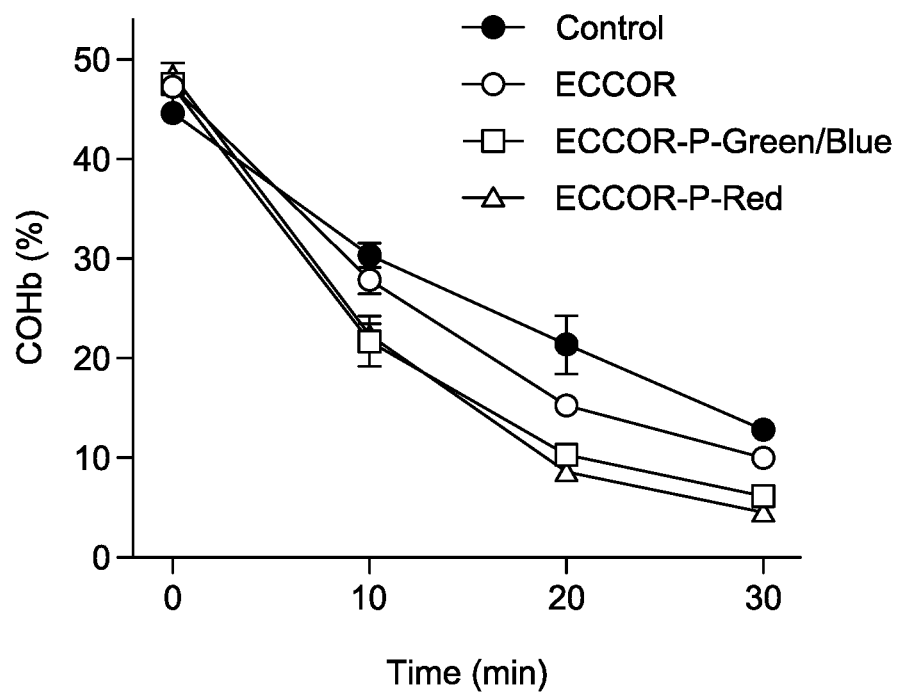
Figure 15:
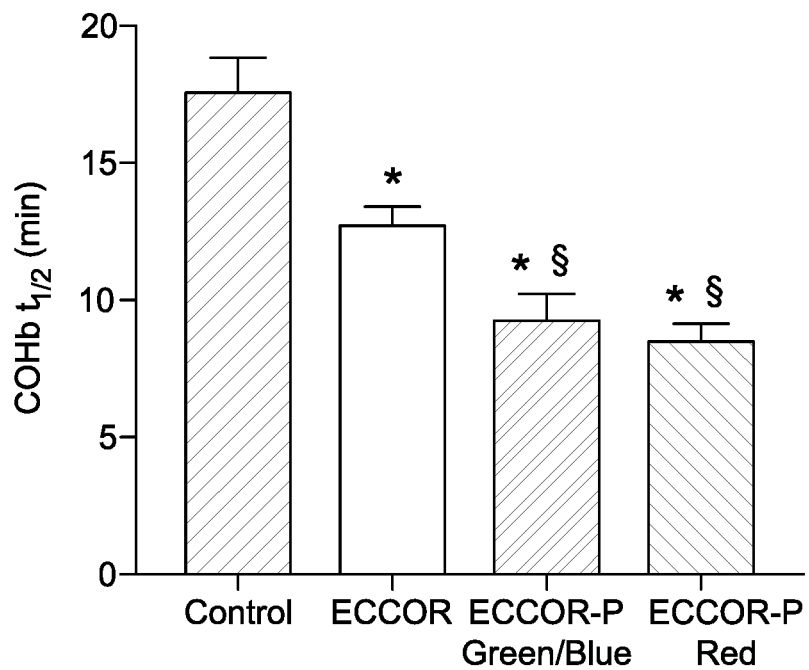

In control animals, neither gas flow nor light was applied to the CO-photo-remover. No CO was eliminated by the device (see FIG. 15A) and the COHb-t$_{1/2}$ was 17.7±1.2 min. Addition of gas flow, but no light, to the CO photo-remover (ECCOR) reduced COHb-t$_{1/2}$ by 28% (12.8±0.6 vs. 17.7±1.2 min, p<0.0001 see FIGS. 15A and 15B). As illustrated in FIGS. 15B-15D, irradiation of the device with green and blue light produced a 47% reduction in COHb-t$_{1/2}$ compared to controls (9.4±0.8 vs. 17.7±1.2 min, p<0.0001) and a 27% reduction in COHb-$_{1/2}$ compared to ECCOR with gas, but without light (9.4±0.8 vs. 12.8±0.6 min p<0.001). Red light produced a 53% reduction in COHb-t$_{1/2}$ compared to control (8.6±0.5 vs. 17.7±1.2 min, p<0.0001) and a 33% reduction in COHb-t$_{1/2}$ compared to ECCOR with gas but without light (8.6±0.5 vs. 12.8±0.6 min, p<0.001). These results show that the extracorporeal removal of CO using phototherapy increases the rate of blood CO elimination in vivo.

Because the CO eliminated by the CO photo-remover during phototherapy (ECCOR-P-Green/Blue and ECCOR-P-Red) was significantly higher than the CO eliminated without phototherapy (ECCOR—only gas flow), there was less CO remaining to be exhaled from the lungs of treated animals compared to control rats (see FIG. 15B). Taken together, these results show that the extracorporeal removal of CO using phototherapy increases the rate of blood CO elimination in vivo.

To determine whether the faster reduction of COHb observed with the combination of ECCOR and phototherapy has a beneficial effect on tissue oxygenation after CO poisoning, a more severe model of CO poisoning was developed. Rats were anesthetized and poisoned by breathing 2000 ppm CO in air for 45 minutes and developed tissue hypoxia and lactic acidosis. During CO poisoning, mean arterial pressure (MAP) decreased from 116±14 to 83±9 mmHg (p<0.0001) and heart rate (HR) increased from 379±38 to 445±40 beats per minute (p<0.0001). Arterial levels of COHb increased to 58.5±1.6% at the end of the CO poisoning period, while venous P02 decreased from 40.8±3.4 to 13.5±2.7 mmHg (p<0.0001). Lactate concentration increased from 2.5±0.5 before CO poisoning to 7.6±0.4 mmol/L (p<0.0001) at the end of 45 minutes and produced acidosis, as suggested by a decreased arterial base excess (from 0.9±1.9 to −7.7±2.3 mmol/L, p<0.0001).

Figure 16:
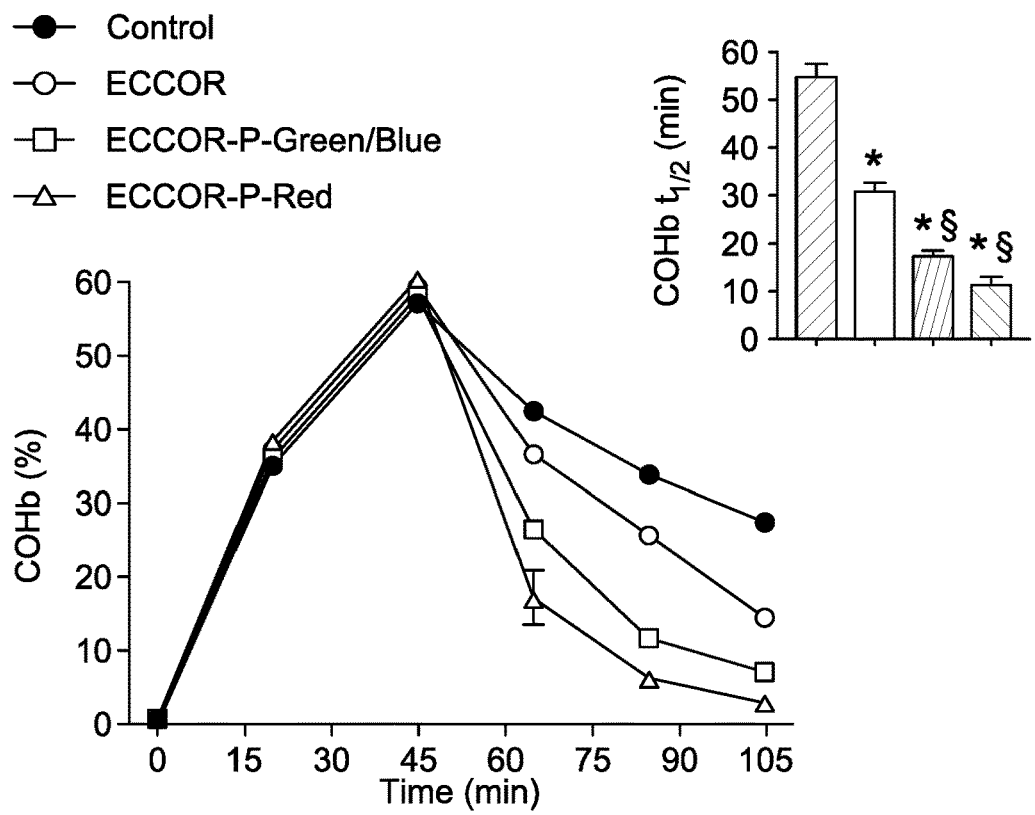
FIG. 16A is a graph illustrating COHb percentage and COHb half-life as a function of time in rats after severe carbon monoxide poisoning with no phototherapy, extracorporeal oxygenation, extracorporeal phototherapy with green/blue light, and extracorporeal phototherapy with red light.
FIG. 16B is a graph illustrating eliminated carbon monoxide from the rats as a function of time in rats after severe carbon monoxide poisoning with no phototherapy, extracorporeal oxygenation, extracorporeal phototherapy with green/blue light, and extracorporeal phototherapy with red light.
FIG. 16C is a graph illustrating eliminated CO from the oxygenator as a function of time in rats after severe carbon monoxide poisoning with no phototherapy, extracorporeal oxygenation, extracorporeal phototherapy with green/blue light, and extracorporeal phototherapy with red light.
FIG. 16D is a graph illustrating normal mixed venous oxygen tension as a function of time in rats after severe carbon monoxide poisoning with no phototherapy, extracorporeal oxygenation, extracorporeal phototherapy with green/blue light, and extracorporeal phototherapy with red light.
FIG. 16E is a graph illustrating lactate as a function of time in rats after severe carbon monoxide poisoning with no phototherapy, extracorporeal oxygenation, extracorporeal phototherapy with green/blue light, and extracorporeal phototherapy with red light.
FIG. 16F is a graph illustrating change in base excess values as a function of time in rats after severe carbon monoxide poisoning with no phototherapy, extracorporeal oxygenation, extracorporeal phototherapy with green/blue light, and extracorporeal phototherapy with red light.
Figure 16:
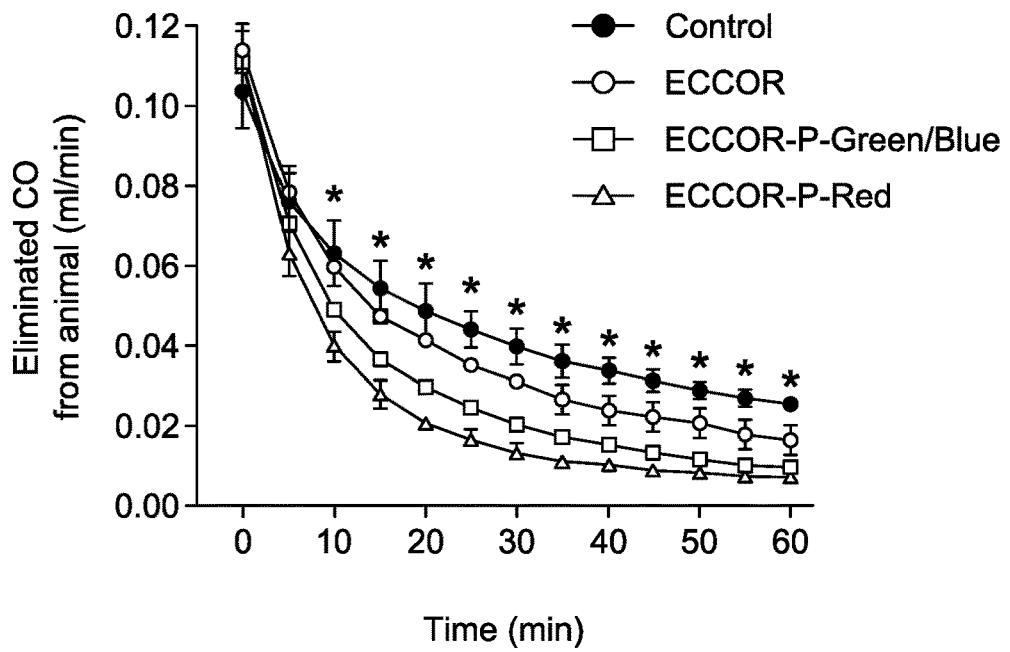
Figure 16:
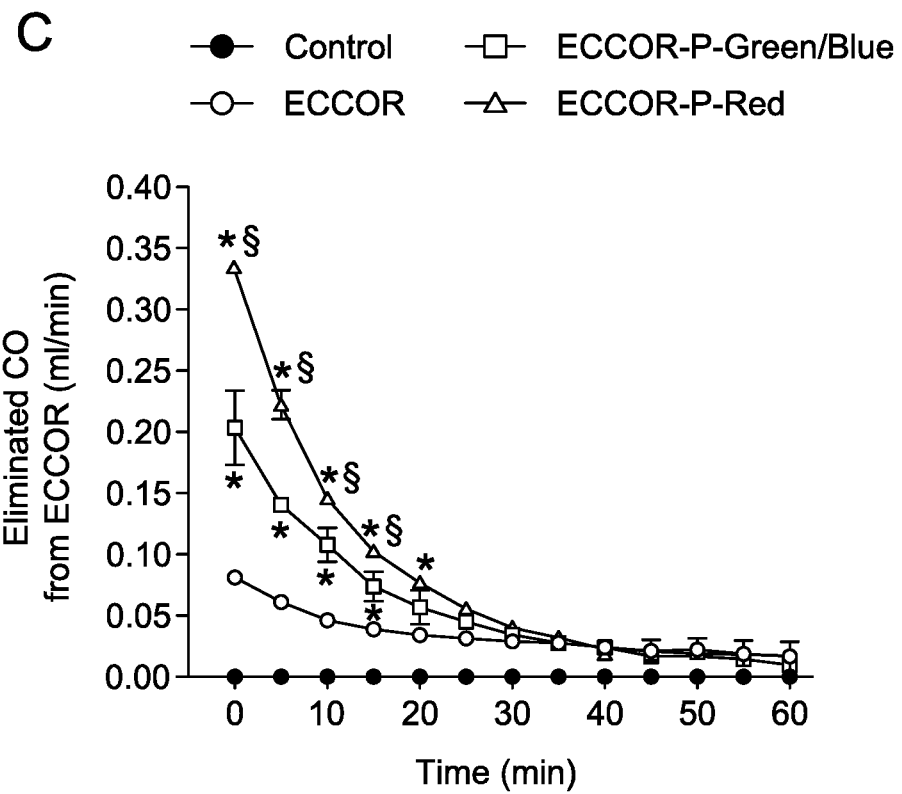
Figure 16:
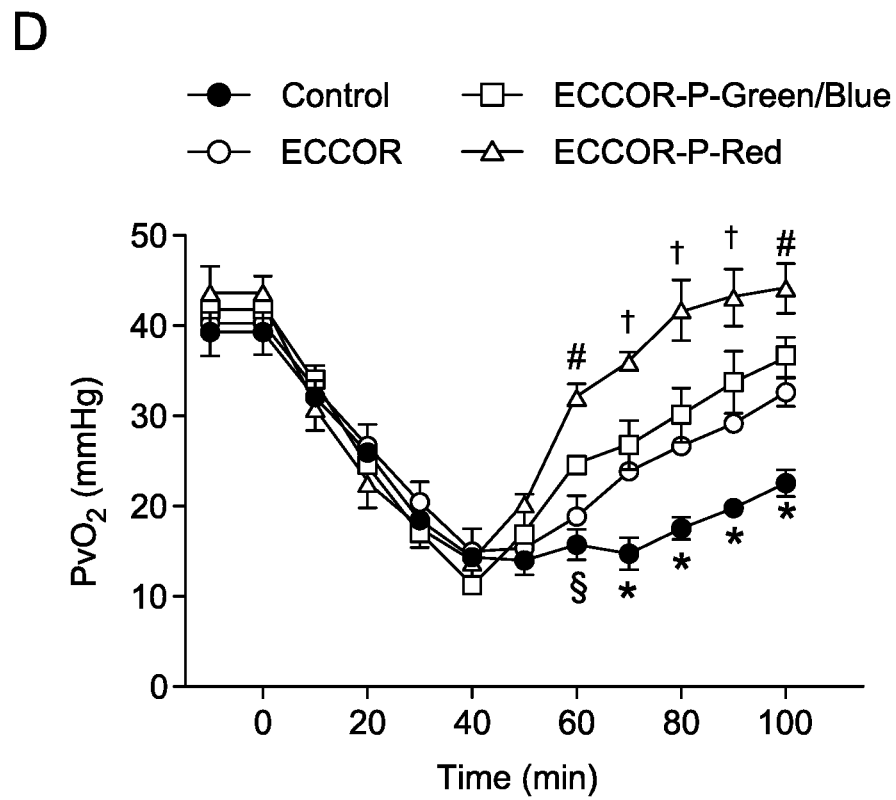
Figure 16:
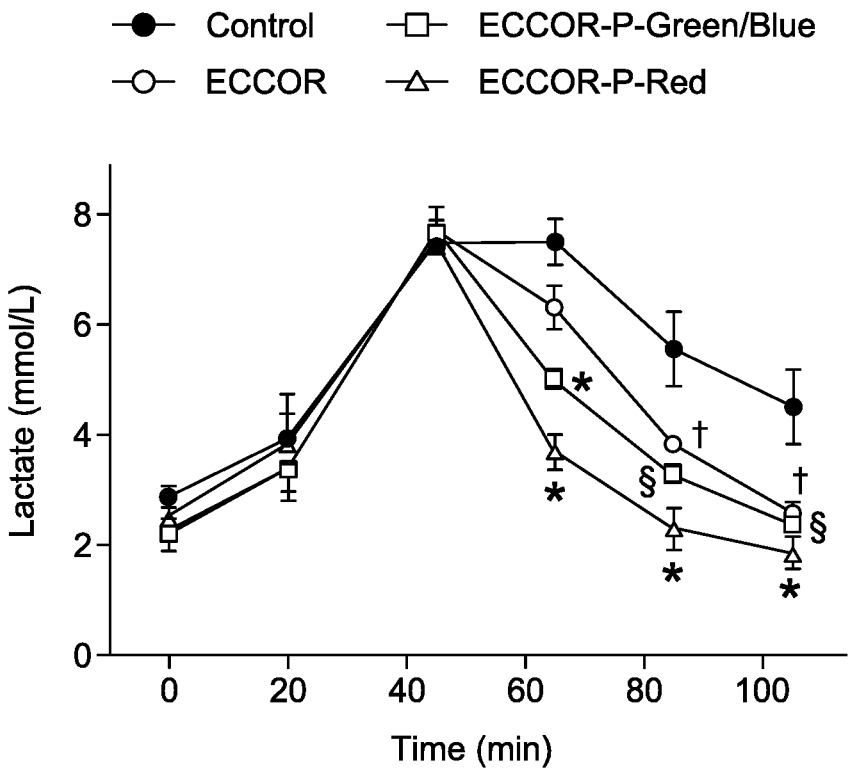
Figure 16:
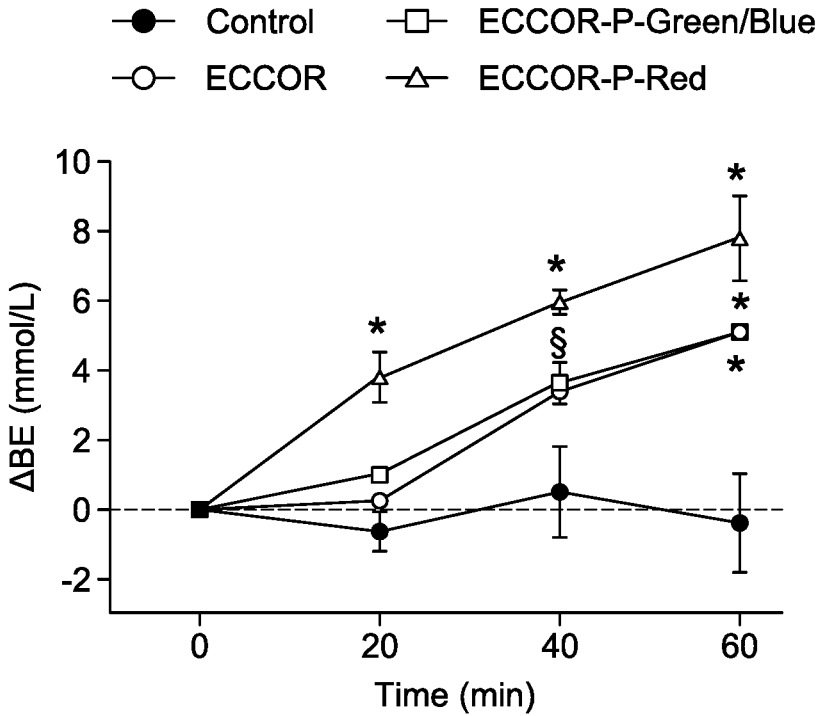

After poisoning, animals were treated by breathing air so as to mimic a situation of reduced arterial oxygenation, as may occur in a patient with acute lung injury (ARDS) and impaired gas exchange. All animals were treated with veno-venous extracorporeal blood circulation with blood flow rates ranging from 50 to 100 ml/kg/min. In control animals the device was provided with neither gas flow nor phototherapy and the COHb-t$_{1/2}$ was 54.9±2.7 min (FIG. 16A). Treatment with ECCOR and gas flow, but no phototherapy, reduced COHb-tv$_{1/2}$ by 44% (54.9±2.7 vs. 31.2±1.5 min p<00001). Treatment with ECCOR, gas flow and combined green and blue light (ECCOR-P-Green/Blue) reduced COHb-tv$_{1/2}$ by 67% compared to control animals (54.9±2 vs. 18.0±0.7 min, p<0.0001). Treatment with ECCOR gas flow and red light (ECCOR-P-Red) reduced COHb-t$_{1/2}$ by 79% compared to controls (54.9±2 vs. 11.6±1.4 min, p<0.0001) and by 35% compared to treatment with ECCOR-P-Green/Blue (18.0±0.7 vs. 11.6±1.4 min, p=0.014).

At the beginning of the treatment period, the elimination of CO from the lungs of CO-poisoned animals was similar in all four groups (FIG. 16B). In later phases of the treatment period, the CO exhaled from the lungs of control animals was higher than in treated animals, as a greater amount of COHb remained in the circulation and more CO was available to be removed by the lungs. The elimination of CO from the CO photo-remover was significantly greater using ECCOR with red light than with ECCOR alone or with ECCOR with green and blue light (see FIG. 16C).

Animals treated with ECCOR-P-Red or ECCOR-P-Green/Blue had a faster return of venous PO$_2$ to baseline (see FIG. 16D) compared to control animals (for which neither gas flow nor phototherapy was applied to the device). Lactate clearance was also faster in ECCOR-P-treated animals (see FIG. 16E), resulting in a more rapid return of base excess to baseline values and correction of metabolic acidosis (see FIG. 16F).

Taken together, these results show that in CO-poisoned rats breathing room air, veno-venous extracorporeal removal of CO using phototherapy dramatically increases the rate of CO elimination and that red light is more effective than the combination of green and blue light in removing CO from the blood of CO poisoned rats. The faster removal of CO from circulating blood is associated with improved tissue oxygenation, as well as faster clearance of systemic lactate and correction of metabolic acidosis.

Figure 17:
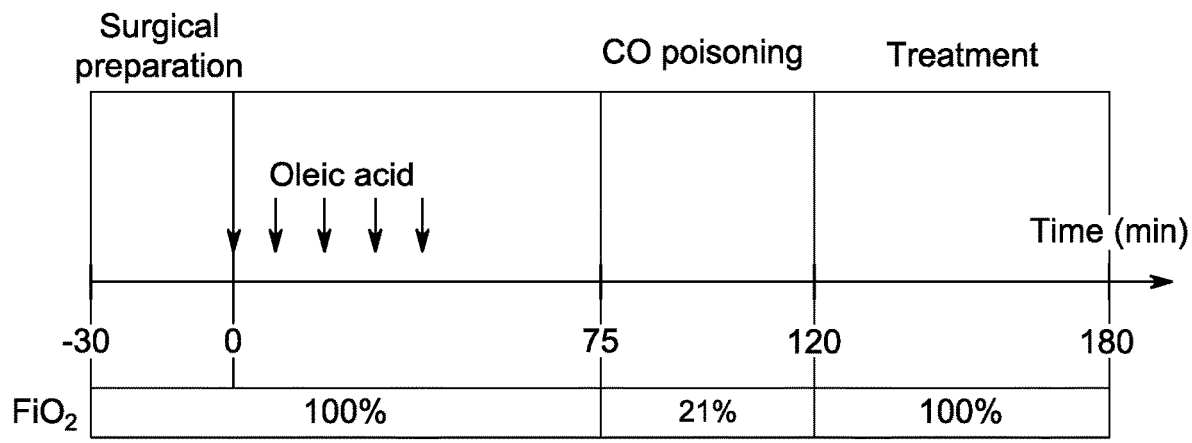
FIG. 17A is a flow chart of lung injury and carbon monoxide poisoning in a rat model.
FIG. 17B is a graph illustrating percent survival after lung injury and carbon monoxide poisoning in rats with no phototherapy and with extracorporeal phototherapy with red light.
FIG. 17C is a graph illustrating a ratio between $PaO_2$ and $FiO_2$ and compliance of the respirator system at baseline and at the end of carbon monoxide poisoning with no phototherapy and with extracorporeal phototherapy with red light.
FIG. 17D is a graph illustrating pH as a function of time after lung injury and carbon monoxide poisoning in rats with no phototherapy and with extracorporeal phototherapy with red light.
FIG. 17E is a graph illustrating partial pressure of oxygen as a function of time after acute lung injury and carbon monoxide poisoning in rats with no phototherapy and with extracorporeal phototherapy with red light.
FIG. 17F is a graph illustrating oxygen hemoglobin percentage as a function of time after acute lung injury and carbon monoxide poisoning in rats with no phototherapy and with extracorporeal phototherapy with red light.
FIG. 17G is a graph illustrating partial pressure of carbon dioxide as a function of time after acute lung injury and carbon monoxide poisoning in rats with no phototherapy and with extracorporeal phototherapy with red light.
FIG. 17H is a graph illustrating mean arterial pressure as a function of time after acute lung injury and carbon monoxide poisoning in rats with no phototherapy and with extracorporeal phototherapy with red light.
FIG. 17I is a graph illustrating heart rate as a function of time after acute lung injury and carbon monoxide poisoning in rats with no phototherapy and with extracorporeal phototherapy with red light.
FIG. 17J is a graph illustrating lactate as a function of time after acute lung injury and carbon monoxide poisoning in rats with no phototherapy and with extracorporeal phototherapy with red light.
FIG. 17K is a graph illustrating COHb percentage as a function of time after acute lung injury and carbon monoxide poisoning in rats with no phototherapy and with extracorporeal phototherapy with red light.
Figure 17:
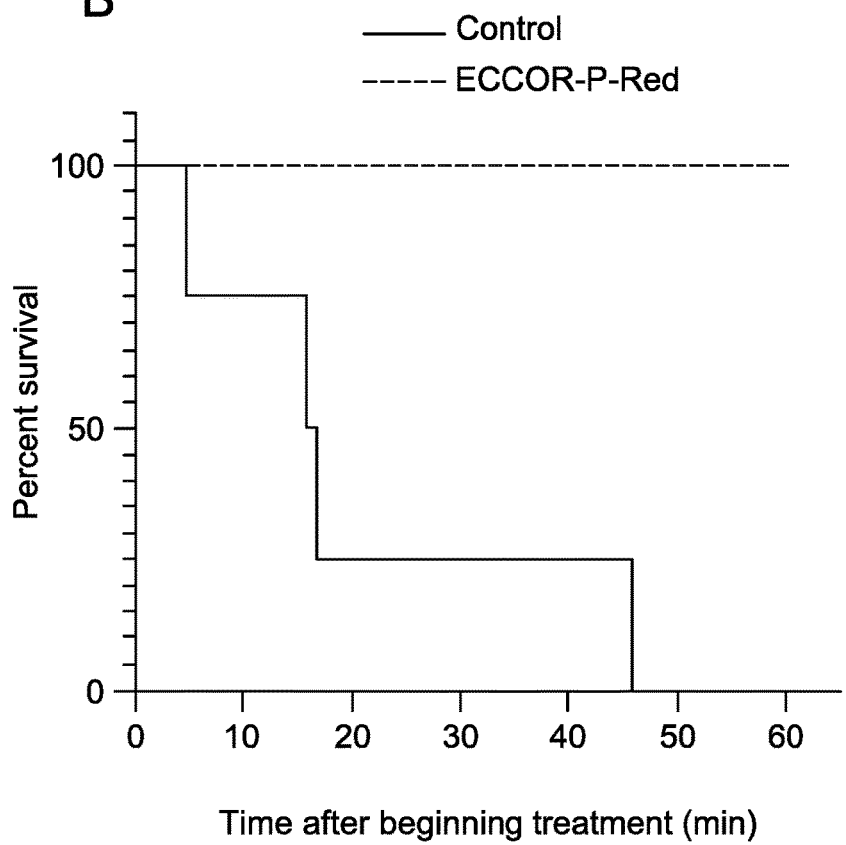
Figure 17:
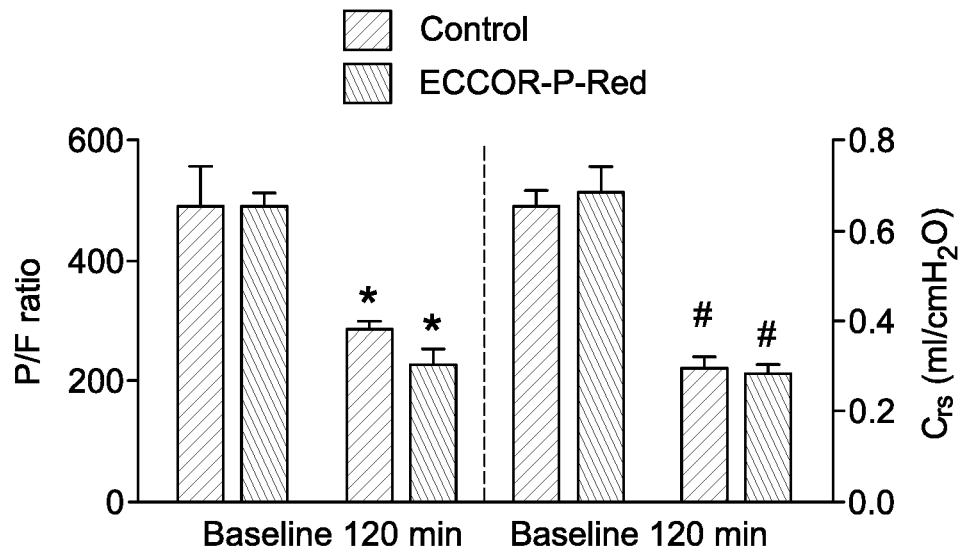
Figure 17:
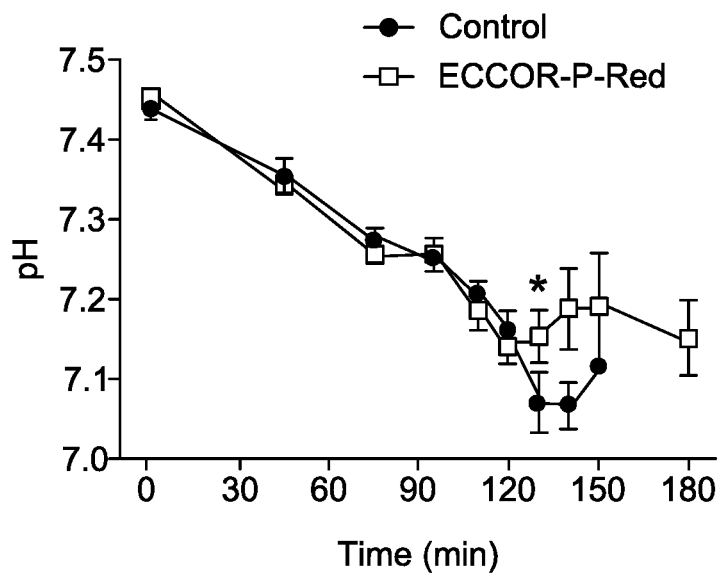
Figure 17:
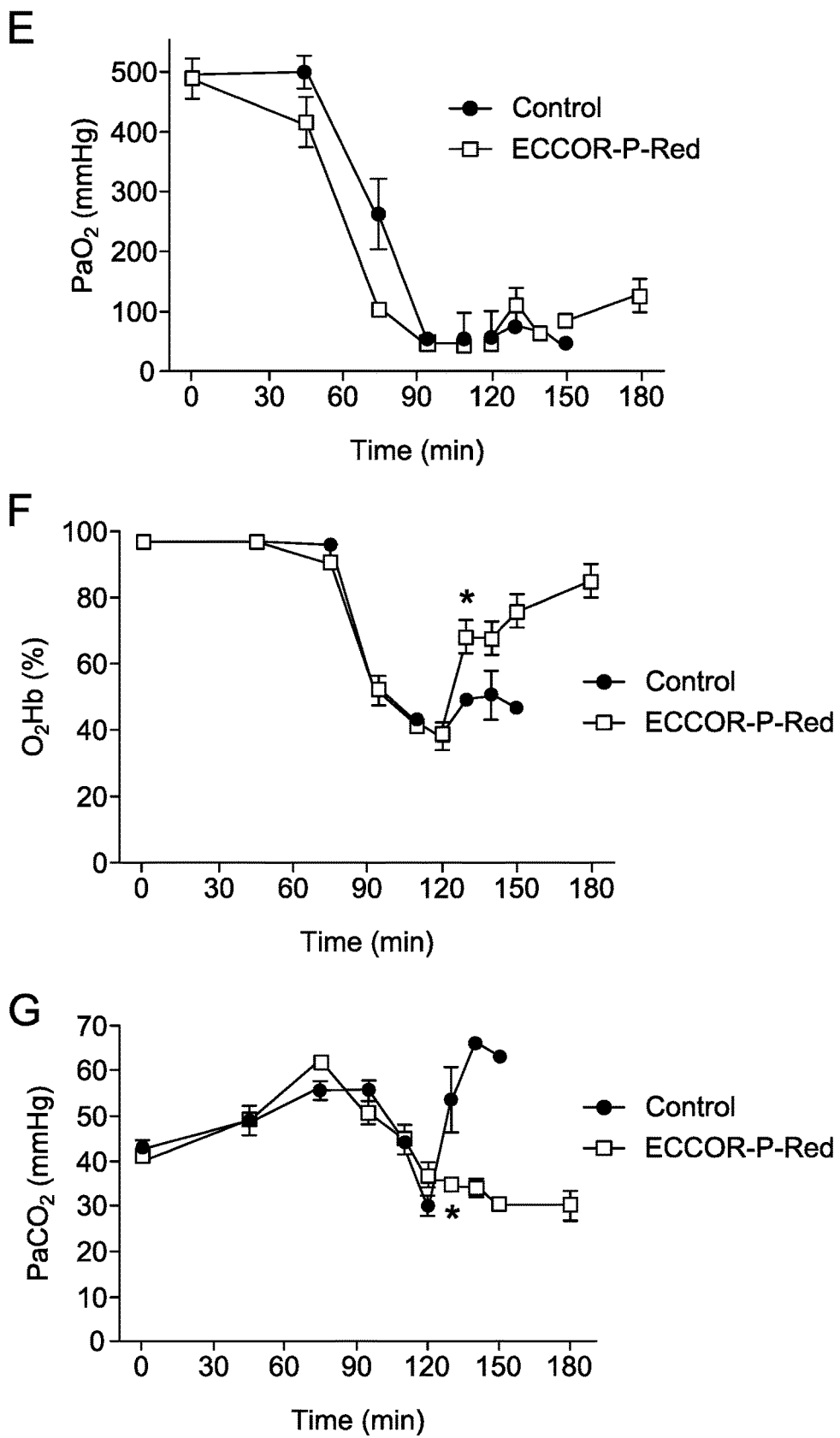
Figure 17:
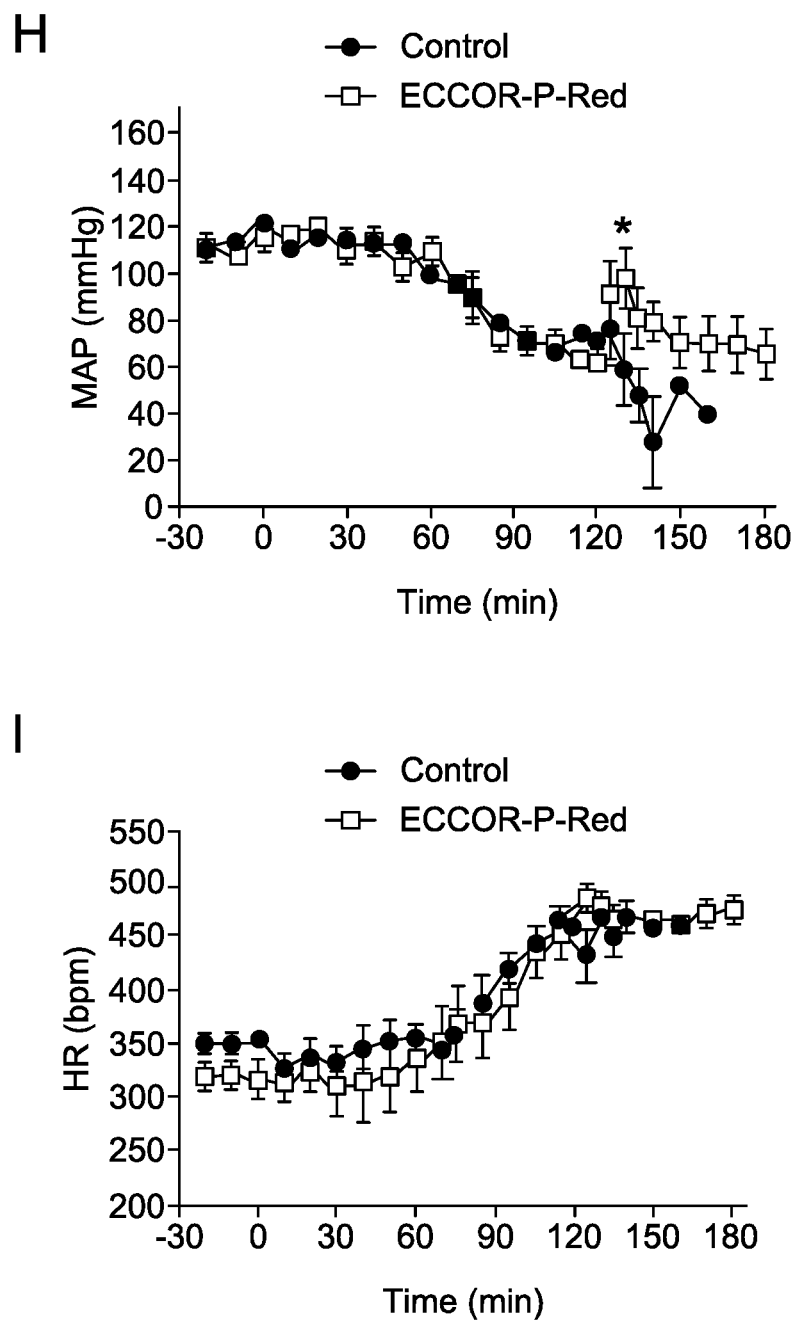
Figure 17:
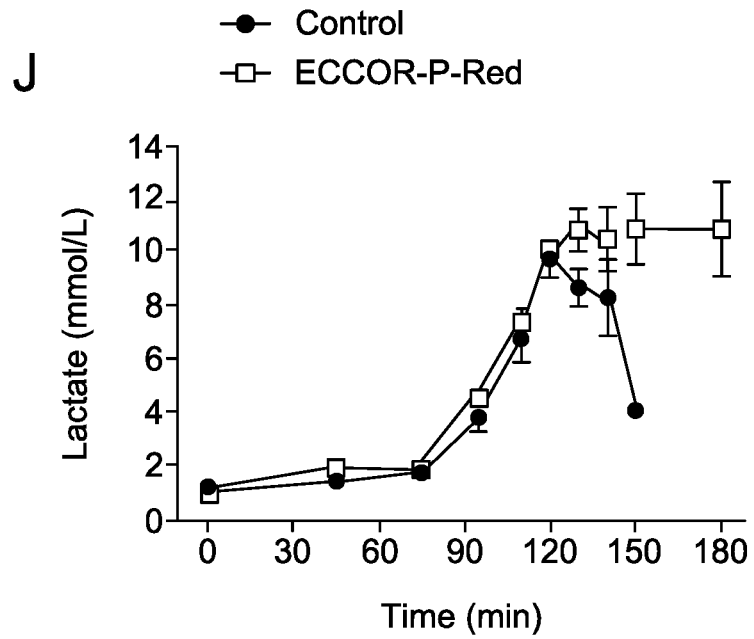
Figure 17:
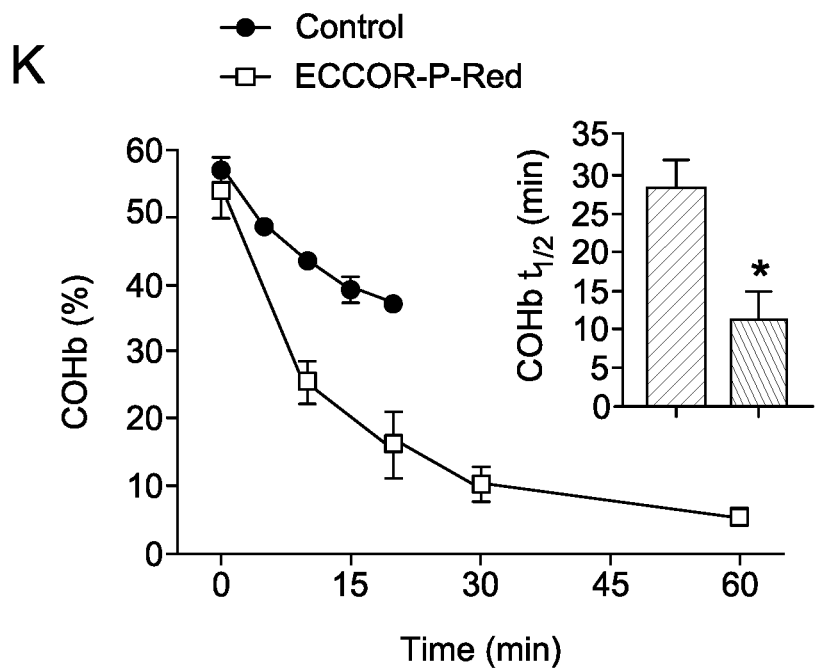

In rats that were poisoned with CO, the use of ECCOR-P-Red doubled the rate of CO elimination compared to rats breathing 100% oxygen and produced a five-fold increase in the rate of CO removal in rats breathing room air. It was hypothesized that ECCOR-P-Red would be particularly beneficial in a situation of limited gas exchange, such as may occur in patients with acute lung injury. An intravenous injection of oleic acid was used to produce a rat model of acute lung injury and impaired gas exchange (see FIG. 17A). This model has a high degree of reproducibility and the histopathological and physiological changes caused by oleic acid are similar to those seen in patients with ARDS. After oleic acid injection, animals were poisoned with 2000 ppm CO for 45 minutes. All of the control animals, treated with 100% oxygen but no extracorporeal circulation, died within 46 minutes after the initiation of treatment. In contrast, all animals treated with 100% oxygen ventilation and ECCOR-P-Red (initiated after the poisoning) survived until the endpoint of the study (60 minutes after the initiation of treatment; see FIG. 17B). The severity of the acute lung injury and the CO poisoning level was comparable in the two groups: 1) The ratio between $PaO_2$ and $FiO_2$ (P/F ratio) and the respiratory system compliance ($C_{rs}$) were significantly reduced at the end of the CO poisoning (and beginning of treatment) in both groups (see FIG. 17C); 2) Arterial pH, $PO_2$ and $O_2Hb$ levels similarly decreased during lung injury and CO poisoning (see FIGS. 17D-17F). The partial pressure of carbon dioxide ($PaCO_2$) initially increased due to lung injury, and then decreased during CO poisoning, likely due to reduced CO2 production in the setting of tissue hypoxia (see FIG. 17G); 3) Prior to treatment, mean arterial pressure, heart rate and the arterial blood lactate levels were similar in both groups (see FIGS. 17H-17L).

In oleic acid treated and CO poisoned rats ventilated with 100% oxygen, the circulating COHb levels decreased faster in rats treated with ECCOR-P-Red than in rats that were treated with 100% oxygen alone. (COHb-$t_{1/2}$: 11.6±2.4 vs. 28.5±3.5 min, p=0002, see FIG. 17M). Compared to control rats, rats treated with ECCOR-P-Red had significantly higher pHa and $O_2Hb$ levels and lower levels of $PaCO_2$ during the treatment period. These results show that, in rats with acute lung injury and CO poisoning, treatment with the veno-venous extracorporeal removal of CO using phototherapy markedly increased the rate of CO elimination and improved overall survival.

Figure 18:
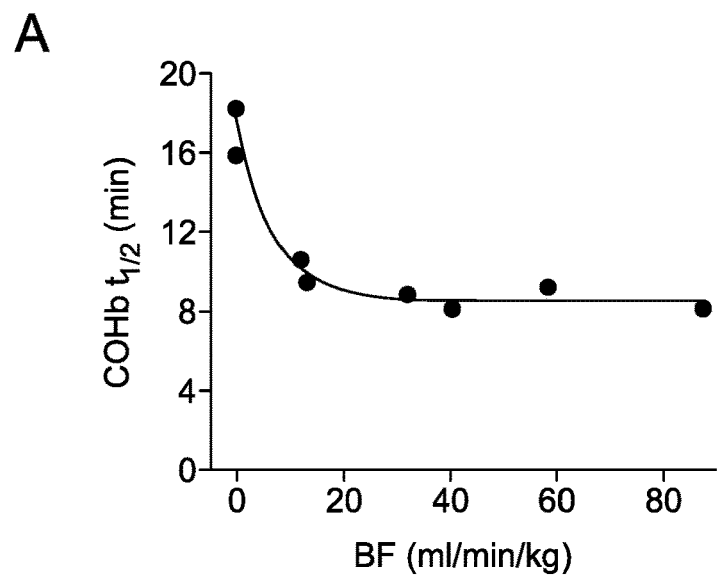
FIG. 18A is a graph illustrating COHb half-life as a function of blood flow rate in carbon-monoxide-poisoned rats with extracorporeal phototherapy with red light and 100% oxygen.
FIG. 18B is a graph illustrating COHb half-life as a function of blood flow rate in carbon-monoxide-poisoned rats with extracorporeal phototherapy with red light and air.
FIG. 18C is a graph illustrating percent carbon monoxide extraction as a function of blood flow rate in carbon-monoxide-poisoned rats with extracorporeal phototherapy with red light.
Figure 18:
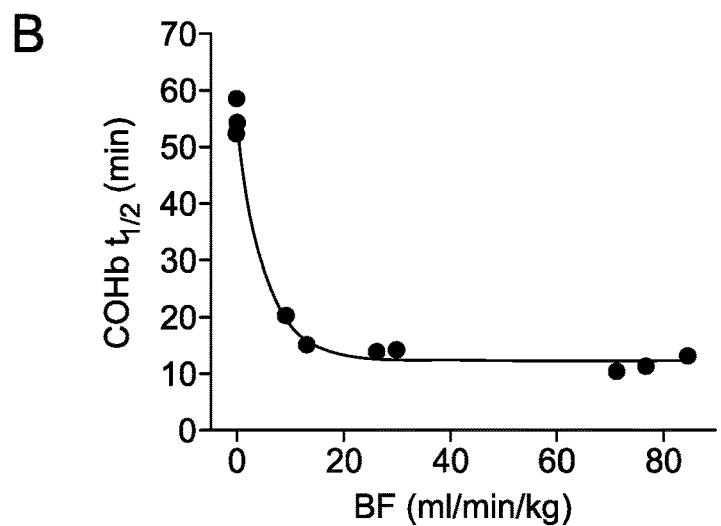
Figure 18:
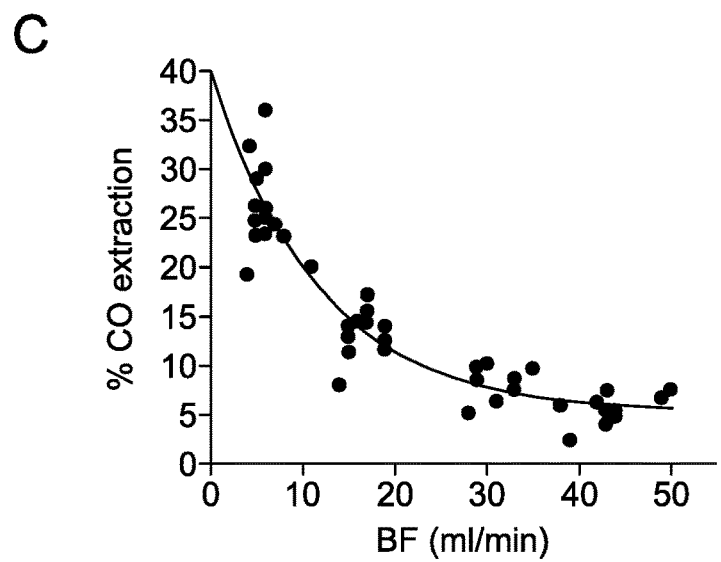

To assess whether the efficacy of CO removal by veno-venous ECCOR-P is altered by changing the rate of blood circulating through the device, rats were poisoned with 2000 ppm CO in air and then treated with 100% oxygen and ECCOR-P-Red at different blood flow rates. Treatment with ECCOR-P-Red increased the rate of CO elimination at blood flows ranging from 10 to 85 ml/kg/min (see FIG. 18A). The relationship between COHb-$t_{1/2}$ and the veno-venous extracorporeal blood flow rate is described by an exponential decay curve (Y=($Y_0$-Plateau)·exp(-K·X)+plateau, (FIG. 6A, $R^2$=0.99). When the blood flow was greater than 20 ml/kg/min (which corresponds to approximately 5-10% of the rat's cardiac output), a CO removal plateau was reached (COHb-$t_{1/2}$ plateau=8.6 min), indicating that a further increase in the blood flow rate did not increase the rate of CO elimination.

To investigate whether ECCOR-P is effective at a wide range of blood flow rates in animals breathing a lower concentration of oxygen, rats were poisoned with 2000 ppm CO in air and then treated by breathing air instead of 100% oxygen. The rats were treated with ECCOR-P-Red at different blood flow rates. ECCOR-P-Red was effective at blood flows ranging from 10 to 85 ml/kg/min, with a COHb-$t_{1/2}$ plateau of 12.4 min (see FIG. 18B, $R^2$=0.97).

At each blood flow rate, the performance of the CO photo-remover was assessed by measuring the amount of CO in the blood entering the device and the amount of CO in the gas effluent. At high blood flow rates, approximately 10% of the CO entering the device was eliminated. In contrast, at lower blood flow rates, up to 35% of the CO entering the device was eliminated (see FIG. 18C). These results show that the extracorporeal removal of CO using phototherapy is highly effective at a wide range of blood flow rates, and that at low blood flow rates more CO is eliminated per unit of blood entering the CO photo-remover.

Blood Temperature as a Function of Treatment Wavelength

The rat-sized CO photo-remover developed as described above was tested to assess the effect of wavelength on blood temperature at the blood outlet port. The size of the blood compartment was 6 cm×6 cm and 8 layers of gas exchange membranes were used. The gas exchange area was 0.05 m². The CO photo-remover was illuminated with 4 LEDs from the top and at the bottom. Blood volume=20 ml, Hb concentration=6.0-7.0 g/dL, blood flow=10 ml/min, gas flow=100 ml/min.

Figure 19:
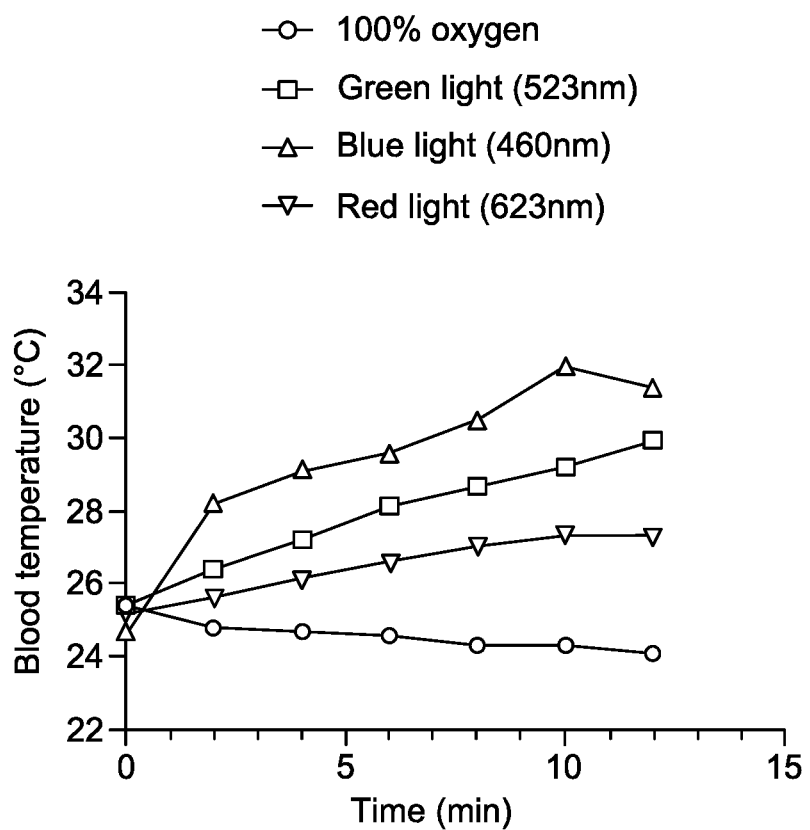
FIG. 19 is a graph illustrating blood temperature as a function of time for extracorporeal oxygenation, extracorporeal phototherapy with green light, extracorporeal phototherapy with blue light, and extracorporeal phototherapy with red light.

As illustrated in FIG. 19, the use of no phototherapy resulted in the blood temperature slightly decreasing over time, while all of the phototherapy tests resulted in an increase in blood temperature. However, the use of red light resulted in the lowest increase in blood temperature, when compared to the use of green light and blue light, which further demonstrates the efficacy of using ECCOR-P treatment with red light to eliminate CO from blood.

CO Removal as a Function of Blood Compartment Layers

Figure 20:
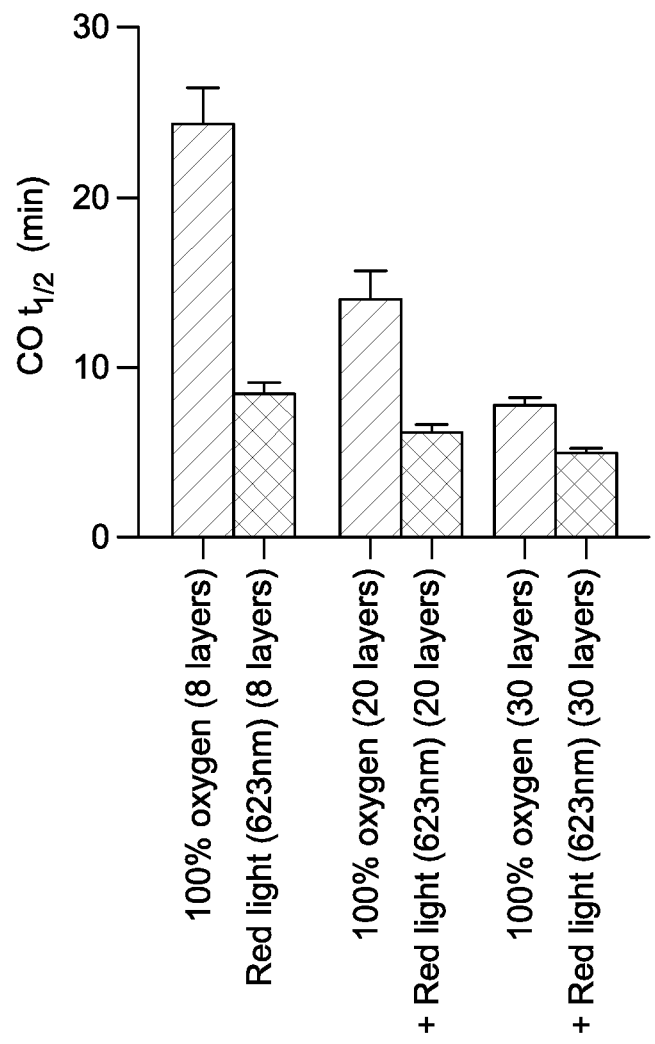
FIG. 20 is a graph illustrating carbon monoxide half-life as a function of a number of layers in a blood compartment of an oxygenator with extracorporeal oxygenation using oxygen and extracorporeal phototherapy using red light.

The rat-sized CO photo-remover developed as described above was tested and in vitro COHb-$t_{1/2}$ was measured during treatment of blood with 100% $O_2$, with or without red phototherapy, with a CO photo-remover having 8, 20, or 30 layers of membranes. As illustrated in FIG. 20, red phototherapy is still effective at CO removal when increasing the blood compartment from 8 layers to 30 layers. The greatest reduction in COHb-$t_{1/2}$, when comparing no red phototherapy to with red phototherapy, is seen for the 8 layer configuration. This is likely due to the ability of the red light to fully penetrate all of the layers of the CO photo-remover. It is hypothesized that there is a maximum thickness where the phototherapy effect diminishes and the light is no longer able to sufficiently penetrate to reach the blood layers. In some non-limiting examples, the number of layers may define a thickness that is less than 10 mm.

Testing a Human-Sized Oxygenator

Experiments were performed with a modified-commercially available oxygenator (Livallova®). The heat exchanger and the blood inflow part were removed from the inside of the oxygenator. A self-made blood inflow part at the other side of the oxygenator was constructed. With these modifications, the oxygenator may be illuminated from the inside and at the outside with red high-power LEDs. The LEDs which are illuminating the inside of the oxygenator are placed on a self-made aluminium box through which cold water runs through. By this, the heat is removed from the oxygenator and the blood does not heat up.

Figure 21:
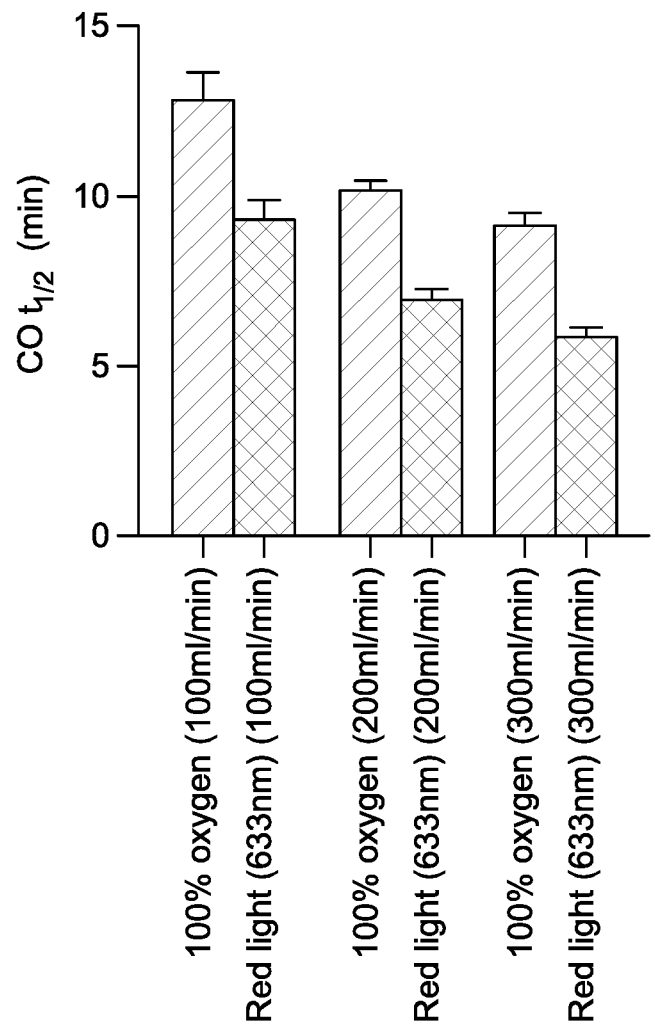
FIG. 21 is a graph illustrating carbon monoxide half-life as a function of blood flow rate in a human-sized oxygenator with extracorporeal oxygenation using oxygen and extracorporeal phototherapy using red light.

As illustrated in FIG. 21, red light at 633 nm was effective at removing CO from the human-sized oxygenator over all of the blood flow rates tested (see FIG. 21). The gas flow rates during the experiments were ten times greater than the illustrated blood flow rates.

Blood Temperature as a Function of Blood Flow Rate with Red Phototherapy

Figure 22:
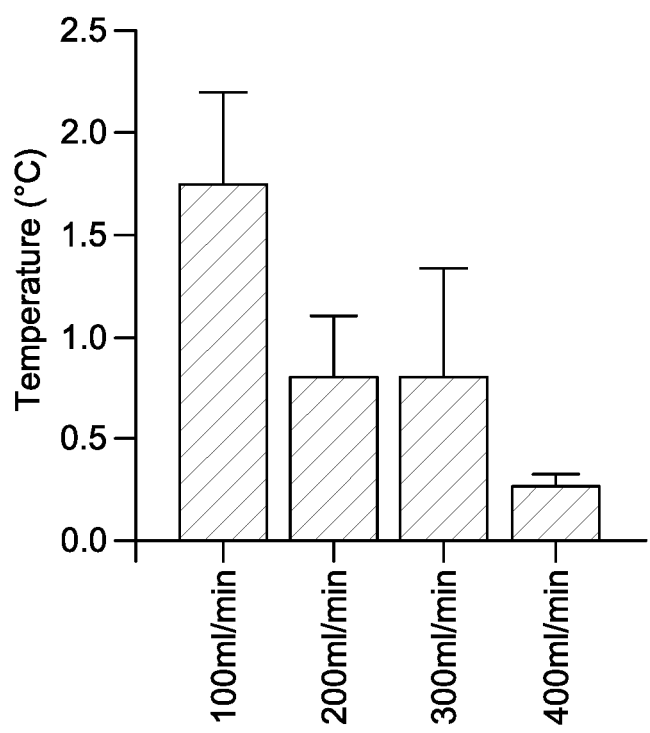
FIG. 22 is a graph illustrating blood temperature increase as a function of blood flow rate in a human-sized oxygenator with extracorporeal phototherapy using red light.

As illustrated in FIG. 22, blood temperature increase was measured using red phototherapy at 623 nm and may be lowered to a medically manageable extent. The results illustrated that blood temperature increase is generally lowered with increasing blood flow rate. However, this trend would need to be balanced with the decreasing CO removal as blood flow increases as discussed herein. In some non-limiting examples, a cooling device may be placed in communication with the blood outlet port to selectively cool the outlet blood to a predetermined temperature.

Flat Human-Sized CO Photo-Remover

Figure 23:
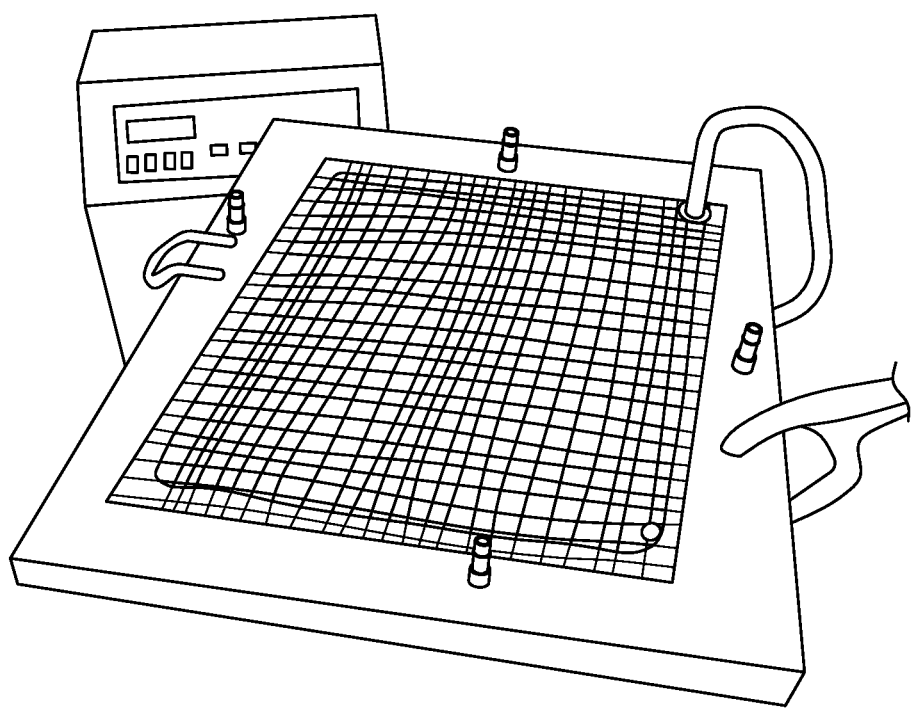
FIG. 23 is a perspective view of a developed human-sized oxygenator.
Figure 24:
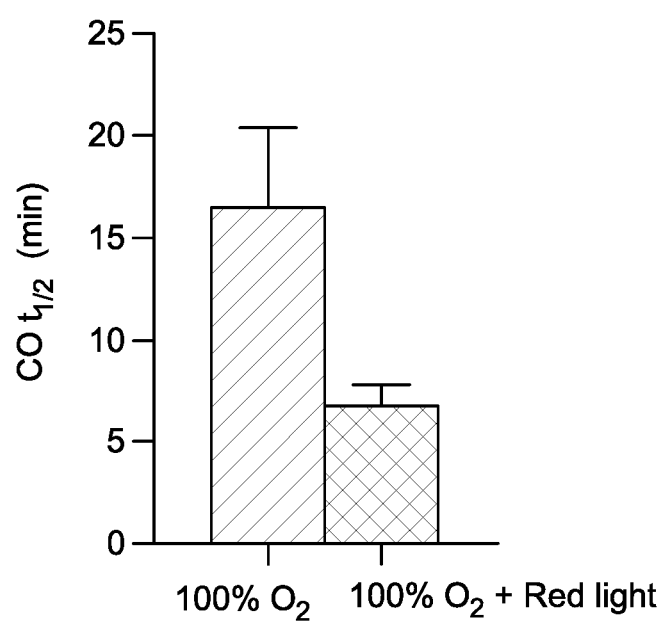
FIG. 24 is a graph illustrating carbon monoxide half-life in the human-sized oxygenator of FIG. 23 with extracorporeal oxygenation using oxygen and extracorporeal phototherapy using red light.

A flat human-sized CO photo-remover was constructed (see FIG. 23). The blood compartment was made with a different gas exchange membrane compared to the previous results (Celgard X30-150 from the company 3M®). Wall thickness=25 µm, outer diameter=200 µm, internal diameter=140 µm. The size of the blood compartment was 19 cm×19 cm. As illustrated in FIG. 24, the human-sized CO photo-remover was effective at significantly reducing COHb-$t_{1/2}$ during treatment of blood with 100% $O_2$ with red phototherapy. Hb=12 g/dl, blood volume=20 ml, blood flow=20 ml/min, gas flow=200 ml/min. Gas exchange area=0.12 $m^2$.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Thus, while the invention has been described in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

We claim:

1. An extracorporeal phototherapy system for removing carbon monoxide from whole blood, the extracorporeal phototherapy system comprising:
   an oxygenator including:
      a plurality of membrane layers each including a plurality of microporous hollow fiber membranes each having an external surface and an internal channel, wherein each of the plurality of membrane layers is rotationally offset with respect to an adjacent layer;
      a gas inlet port in fluid communication with a first end of the internal channels;
      a gas outlet port in fluid communication a second end of the internal channels;
      a blood inlet port in fluid communication with the external surfaces; and
      a blood outlet port in fluid communication with the external surfaces; and
   a light source configured to output light and arranged to emit the light output by the light source onto at least one surface of the oxygenator, wherein the light source is configured to emit light with a wavelength greater than 600 nanometers.

2. The extracorporeal phototherapy system of claim 1, wherein the adjacent layers of the plurality of microporous membrane layers are offset ninety degrees from one another.

3. The extracorporeal phototherapy system of claim 1, wherein the oxygenator includes a housing enclosing the plurality of membrane layers, and wherein the housing is fabricated from a material configured to transmit light emitted from the light source therethrough.

4. The extracorporeal phototherapy system of claim 3, wherein the housing and the plurality of membrane layers define a planar shape or a cylindrical shape.

5. The extracorporeal phototherapy system of claim 3, wherein the gas inlet port, the gas outlet port, the blood inlet port, and the blood outlet port are formed in the housing.

6. The extracorporeal phototherapy system of claim 1, wherein the gas inlet port is configured to receive a flow of oxygen and the blood inlet port is configured to receive a flow of whole blood, and wherein the flow of oxygen and the flow of whole blood are in a common direction.

7. The extracorporeal phototherapy system of claim 6, wherein a ratio of a gas flow rate of the gas flow to a blood flow rate of the flow of blood is greater than or equal to 5:1.

8. The extracorporeal phototherapy system of claim 1, further comprising a cooling device in fluid communication with the blood outlet port.

9. The extracorporeal phototherapy system of claim 1, wherein the plurality of membrane layers define a thickness less than 10 millimeters.

10. An extracorporeal phototherapy system for removing carbon monoxide from whole blood, the extracorporeal phototherapy system comprising:
   an oxygenator including:
      a plurality of membrane layers;
      a gas inlet port configured to provide fluid communication through internal channels formed in each of the plurality of membrane layers and to a gas outlet port; and
      a blood inlet port configured to provide fluid communication around external surfaces defined by each of the plurality of membrane layers and to a blood outlet port;
   a first light source configured to output light and arranged to emit the light output by the first light source onto a first side of the oxygenator; and
   a second light source configured to output light and arranged to emit the light output by the second light source onto a second side of the oxygenator opposite to the first side, wherein the first light source and the second light source are configured to emit light with a wavelength greater than 600 nanometers.

11. The extracorporeal phototherapy system of claim 10, wherein adjacent layers of the plurality of microporous membrane layers are offset ninety degrees from one another.

12. The extracorporeal phototherapy system of claim 10, wherein the plurality of membrane layers each include a plurality of microporous hollow fiber membranes.

13. The extracorporeal phototherapy system of claim 10, wherein the oxygenator includes a housing enclosing the plurality of membrane layers, and wherein the housing is fabricated from a material configured to transmit light emitted from the light source therethrough.

14. The extracorporeal phototherapy system of claim 13, wherein the housing and the plurality of membrane layers define a planar shape or a cylindrical shape.

15. The extracorporeal phototherapy system of claim 13, wherein the gas inlet port, the gas outlet port, the blood inlet port, and the blood outlet port are formed in the housing.

16. The extracorporeal phototherapy system of claim 10, wherein the gas inlet port is configured to receive a flow of oxygen and the blood inlet port is configured to receive a flow of whole blood, and wherein the flow of oxygen and the flow of whole blood are in a common direction.

17. The extracorporeal phototherapy system of claim 16, wherein a ratio of a gas flow rate of the gas flow to a blood flow rate of the flow of blood is greater than or equal to 5:1.

18. The extracorporeal phototherapy system of claim 10, further comprising a cooling device in fluid communication with the blood outlet port.

19. The extracorporeal phototherapy system of claim 10, wherein the plurality of membrane layers define a thickness less than 10 millimeters.

* * * * *